United States Patent
Schmidt et al.

(10) Patent No.: US 6,603,062 B1
(45) Date of Patent: Aug. 5, 2003

(54) METHOD FOR PRODUCING TRANSGENIC PLANTS WITH MODIFIED 5-AMINOLEVULINIC ACID BIOSYNTHESIS, METHOD FOR IDENTIFYING 5-AMINOLEVULINIC ACID SYNTHESIS EFFECTORS

(75) Inventors: Frank Schmidt, Frankfurt (DE); Günter Donn, Hofheim (DE)

(73) Assignee: Aventis CropScience GmbH, Berlin (DE)

( * ) Notice: Subject to any disclaimer, the term of this patent is extended or adjusted under 35 U.S.C. 154(b) by 0 days.

(21) Appl. No.: 09/581,105

(22) PCT Filed: Dec. 10, 1998

(86) PCT No.: PCT/EP98/08028

§ 371 (c)(1),
(2), (4) Date: Aug. 31, 2000

(87) PCT Pub. No.: WO99/29880

PCT Pub. Date: Jun. 17, 1999

(30) Foreign Application Priority Data

Dec. 10, 1997 (DE) .......................... 197 54 929

(51) Int. Cl.$^7$ ............................ A01H 5/00; A01H 5/10; C12N 15/82; C12N 15/31
(52) U.S. Cl. ................... 800/300; 47/58.1; 435/320.1; 435/468; 435/418; 435/419; 435/412; 435/413; 536/23.7; 800/278; 800/298; 800/300.1; 800/320.1; 800/288
(58) Field of Search ................. 435/468, 418, 435/419, 320.1; 800/278, 288, 286, 298, 300, 300.1, 320.1; 536/23.2, 23.5, 23.7; 47/58.1

(56) References Cited

FOREIGN PATENT DOCUMENTS

| WO | WO 97/20209 | 6/1997 |
|----|-------------|--------|
| WO | WO 98/24920 | 6/1998 |

OTHER PUBLICATIONS

Zavgorodnyaya et al. 1997, Yeast 5–aminolevulinate synthase provides additional chlorophyll precursor in transgenic tobacco. The Plant Journal 12(1): 169–178.*

Tan et al. 1996, Active site of 5–aminoevulinate synthase resides at the subunit interface. Evidence from in vivo heterodimer formation. Biochemistry 35:8934–8941.*

Tan et al, Active Site of 5–Aminolevulinate Resides at the Subunit Interface, Nov. 1996, Biochemistry, vol. 35, pp. 8934–8941.*

Tyacke et al., Biochem. J., vol. 309, pp. 307–313, 1995.

Hoober et al., Carlsberg Res. Commun., vol. 53, pp. 11–25, 1988.

Wang, Enviornmental Research, vol. 52, pp. 7–22, 1990.

Allison et al., Mol. Gen. Genet., vol. 255, pp. 392–399, 1997.

Zavgorodnyaya et al., The Plant Journal, vol. 12, No. 1, pp. 169–178, 1997.

Gough et al., Target Assays for Modern Herbicides and Related Phytotoxic Compounds, Chapter 4, pp. 21–27, 1993.

Abell, Weed Science, vol. 44, pp. 734–742, 1996.

Foster et al., BCPC Monograph No. 55: Opportunities For Molecular Biology in Crop Production, pp. 75–81, 1993.

Hofgen et al., Proc. Natl. Acad. Sci. USA, vol. 91, pp. 1726–1730, 1994.

Neidle et al, Journal of Bacteriology, vol. 175, No. 8, pp. 2292–2303, 1993.

* cited by examiner

Primary Examiner—David T. Fox
Assistant Examiner—David H Kruse
(74) Attorney, Agent, or Firm—Frommer Lawrence & Haug LLP

(57) ABSTRACT

Provided is a method for producing transgenic monocotyledonous plants, plant cells, plant parts, seeds, and reproduction material with modified 5-aminolevulinic acid biosynthesis. This is achieved by stably integrating one or several nucleic acid molecules coding for a protein with a 5-aminolevulinic acid synthase function (ALAS) isolated from the alpha group of purple bacteria, an active fragment thereof or an antisense or complementary sequence thereof, into tie plant genome in stable form. This method can also be used to control undesired vegetation Also provided is a method for producing transgenic plants or plant cells whose glutamate-1-semialdehyde transferase (GSAAT) expression is suppressed or inhibited by stable integration of at least one nucleic acid molecule encoding an ALAS isolated from the alpha group of purple bacteria into the plant plastome by plastid transformation.

20 Claims, 3 Drawing Sheets

METHOD FOR PRODUCING TRANSGENIC PLANTS WITH MODIFIED 5-AMINOLEVULINIC ACID BIOSYNTHESIS, METHOD FOR IDENTIFYING 5-AMINOLEVULINIC ACID SYNTHESIS EFFECTORS

CROSS-REFERENCE TO RELATED APPLICATIONS

This application claims the benefit of and priority to PCT Applications PCT/EP98/08028 filed Dec. 10, 1998 designating the U.S., which claims priority from German Patent Application 197 54 929.2 filed Dec. 10, 1997. Each of these documents is incorporated herein by reference.

STATEMENT REGARDING FEDERALLY SPONSORED RESEARCH AND DEVELOPMENT

Not applicable.

BACKGROUND OF THE INVENTION

The invention relates to methods for producing transgenic plant cells and plants with modified 5-aminolevulinic acid biosynthesis, to the use of nucleic acid molecules encoding a protein which act as a 5-aminolevulinic acid synthase (ALAS) for producing transgenic plant cells and plants, methods for identifying effectors, and the use of effectors, of aminolevulinic acid biosynthesis, in particular the use of herbicidally active inhibitors of plant 5-aminolevulinic acid biosynthesis in crops, preferably in transgenic crops.

Herbicides are used widely in modern agriculture for controlling undesired vegetation on agricultural land. Despite the use of herbicides, an efficient control of weeds and harmful plants is not always possible in a satisfactory manner since highly effective herbicides which have a broad spectrum of action are frequently not tolerated by useful plants, or else the development of resistance phenomena can be observed.

So far, it has been attempted to circumvent these disadvantages by useful plants which tolerate herbicides with a non-selective action. The herbicide tolerance can be generated by modifying the plant enzyme which is inhibited by the selected herbicide in such a way that it is less sensitive to the herbicidally active substance. For example, WO 95/3459 describes plants which express genes of protoporphyrinogen oxidase variants and thus have an increased tolerance to herbicidal diphenyl ethers and other inhibitors of plant protoporphyrinogen oxidase.

Herbicide tolerance was also achieved by introducing, by genetic engineering, enzymes into the metabolism of crop plants which are capable of deactivating the herbicidally active substance applied (for example EP-A-0 242 236; EP-A-0 343 100).

CONFIRMATION COPY

It is known that the biosynthesis of 5-aminolevulinic acid (ALA) is a rate-determining and regulatory metabolic step for porphyrin synthesis in plants, animals, fungi and bacteria. In plants and in most prokaryotes, with the exception of the alpha group of the purple bacteria, ALA is produced from glutamate via the so-called C5 metabolic pathway. The C5 metabolic pathway (C5 pathway) consists of three reaction steps which are catalyzed by the enzymes glutamyl-tRNA synthetase (EC 6.1.1.17), glutamyl-tRNA reductase (EC 1.2.1.-.) and glutamate-1-semialdehyde aminotransferase (GSAAT, EC 5.4.3.8.) and, in plants, is localized in the plastids.

GSAAT has been isolated from a variety of organisms, and the structural genes of the enzyme have been cloned for example from the plants *Arabidopsis thaliana*, tobacco, barley and soybean.

Plant GSAAT can be produced by recombinant technology by means of heterologous expression of its cDNA (Berry-Lowe et al. (1992) Plant Physiol. 99: 1597–1603).

GSAAT is inhibited by 3-amino-2,3-dihydrobenzoic acid. After application of 3-amino-2,3-dihydrobenzoic acid, the treated plants are incapable of synthesizing ALAs and thus no longer the porphyrin compounds chlorophyll, heme and siroheme (Beale (1990) Plant Physiology 93: 1273–1279). Such plants develop highly chlorotic tissue which is destroyed when exposed to light.

An alternative biosynthetic pathway for the production of ALA exists in animals, fungi, yeasts and the purple bacteria of the alpha group, for example *Rhodobacter sphaeroides* or *Rhodobacter capsulatus*. In this synthetic pathway, which is termed Shemin metabolic pathway, succinyl-CoA and glycine are condensed in a single reaction step which is catalyzed by the enzyme 5-aminolevulinic acid synthase (ALAS, EC 2.3.1.37.), to give ALA (Kikuchi et al. (1958) Journal of Biological Chemistry 233: 1214–1219). In eukaryotes, the reaction steps of the Shemin metabolic pathway proceed in the mitochondria.

ALAS has been isolated from a number of organisms. The ALAS structural gene has been isolated, inter alia, from *Saccharomyces cerevisiae, Rhodobacter sphaeroides, Rhodobacter capsulatus*, humans and mice.

ALAS, being the first enzyme of the Shemin tetrapyrrole biosynthesis pathway, has already been examined early for its regulation at the transcriptional level and at the enzyme activity level (Lascelles (1968) Biochem. Soc. Symp. 28: 49–59, Gamick et al. (1975) Journal of Biological Chemistry 250: 9215–9225). It has been found in particular in the case of prokaryotic 5-aminolevulinate synthases that heme is an important direct feedback regulator of enzyme activity.

It was an object to provide a resistance principle to plant 5-amino acid levulinic acid synthesis inhibitors which is suitable under practice conditions and to provide a rational method for finding such inhibitors which is suitable for practice conditions.

The introduction of a heterologous ALAS activity in tobacco plants using the cDNA of Saccharomyces cerevisiae ALAS (SEQ ID NO: 4) has already been described by Zavgorodnyaya et al. (1997, Plant Journal 12, 169–178).

However, the ALA synthesis rate in the plant must be sufficient to ensure the ALA requirement for the physiologically necessary porphyrin biosynthesis. On the other hand, ALA production must not be so high as to damage the plant directly or indirectly. This is why the C5 biosynthesis pathway for ALA is regulated in plants.

Similarly, it must be guaranteed that the ALA synthesis in the transgenic plants which contain a heterologous ALAS activity does not have detrimental consequences for the plants.

Surprisingly, it has now been found that plants can be produced which are resistant to herbicidally active inhibitors of the C5 metabolic pathway, for example to GSAAT inhibitors, when certain heterologous ALAS genes are expressed, in useful plants, in substitutive or complementary fashion so that non-selectively acting inhibitors of the C5 metabolic pathway can be employed in said transgenic crops of useful plants as herbicides.

BRIEF SUMMARY OF THE INVENTION

The present invention therefore provides a method for producing transgenic plants with modified 5-aminolevulinic acid biosynthesis in which the metabolic pathway which is inhibited specifically by a herbicide is circumvented by a heterologous gene expression which complements or substitutes the inhibition. For a suitable complementation or substitution, the plants are equipped, by means of one or more heterologous nucleic acid molecules, with one or more additional or alternative biosynthetic steps which lead to the end product of the inhibited metabolic pathway so that a resistance of the transgenic plant to the herbicidally active inhibitor of the C5 metabolic pathway results.

DETAILED DESCRIPTION OF THE INVENTION

Figure 1:
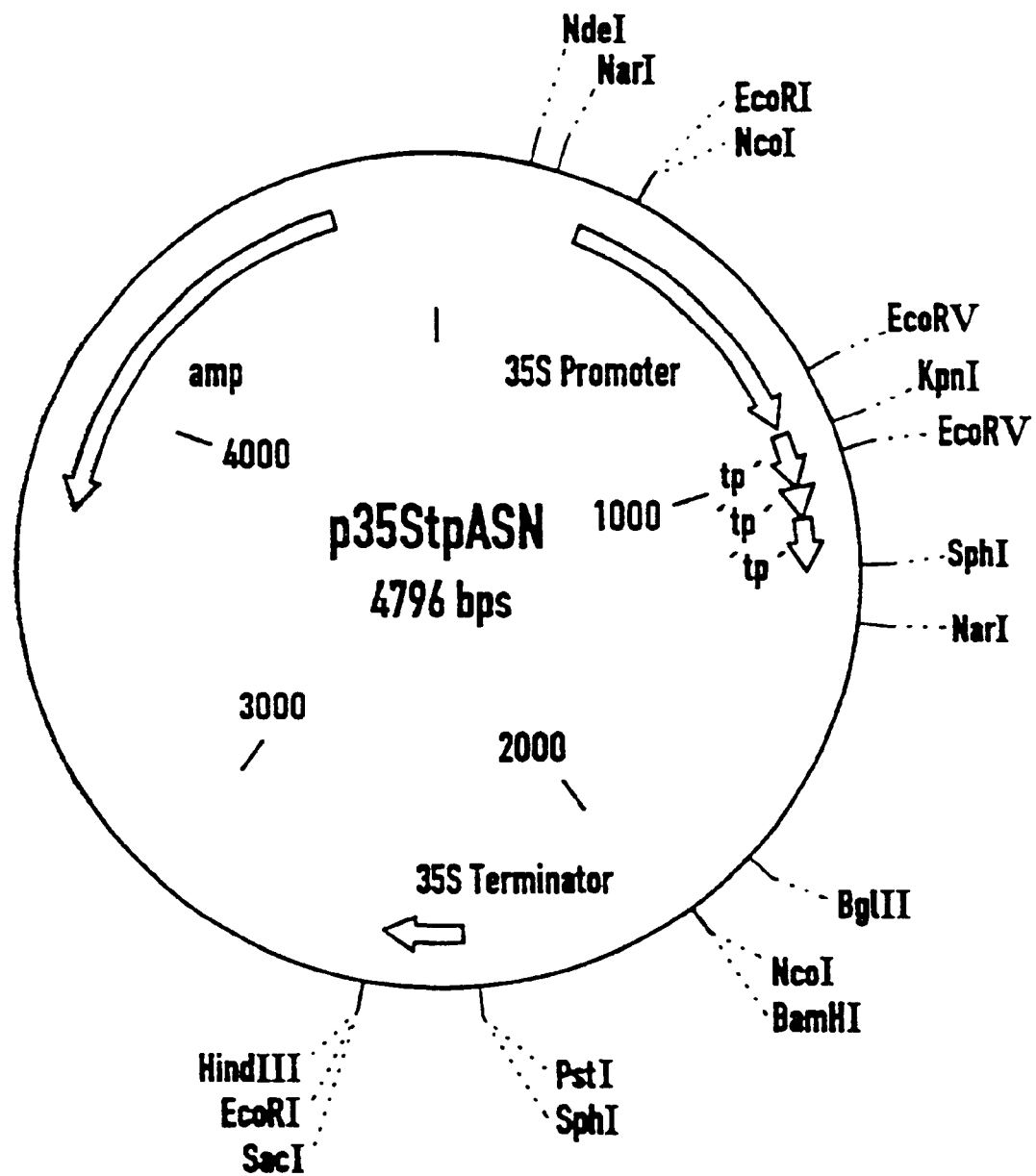
FIG. 1 depicts lasmid p35StpASN.

In plants, ALA biosynthesis proceeds exclusively via the C5 pathway, which is localized in the chloroplasts. Surprisingly, it has now been found that transgenic plants which contain a heterologous ALAS activity are capable of producing aminolevulinic acid for chlorophyll and heme-biosynthesis independently of the activity of the C5 pathway.

This alternative metabolic pathway imparts, to the transgenic plants which exhibit ALAS activity, the desired resistance to non-selective herbicides which inhibit aminolevulinic acid formation within the C5 pathway, for example by inhibition of the enzyme GSAAT, by means of circumventing the metabolic step which is blocked by the herbicidal active substance. A resistance by means of the heterologous ALAS activity can be obtained in the transgenic plants also to glutamyl-tRNA reductase inhibitors.

The invention therefore relates to a method for producing transgenic plants, transgenic plant cells, transgenic plant parts, transgenic plant seeds, and transgenic propagation material with modified 5-aminolevulinic acid biosynthesis containing one or more functionally active nucleic acid molecules encoding a protein with the function of an ALAS selected from the group of the feedback-regulated ALASs, animal ALASs and bacterial ALASs, preferably a feedback-regulated ALAS, especially preferably purple bacteria ALAS, active fragments thereof or an antisense or complementary sequence thereof, which are stably integrated into the plant genome by a method known per se for the production of transgenic plant cells or plants, plant parts, plant seeds or propagation material.

Genome for the purposes of the present invention includes the entire genetic material of a plant, i.e. also the genetic material of all organelles of the plant cells, in addition to the nuclear DNA.

Equally surprisingly, it has been found that monocotyledonous plants, in particular maize plants, can be produced which are resistant to herbicidally active inhibitors of the C5 metabolic pathway, for example to GSAAT inhibitors, when, in these useful plants, heterologous ALAS genes are expressed in a substitutive or complementary manner so that non-selectively acting inhibitors of the C5 metabolic pathway can be employed as herbicides in said transgenic crops of useful plants.

This was all the more surprising as it is known to the skilled worker that, owing to the important differences between monocotyledonous and dicotyledonous plants, effects which are observed in dicotyledonous plants can generally not simply be applied in their entirety to monocotyledonous plants.

The invention therefore furthermore relates to a method for producing transgenic plants, transgenic plant cells, transgenic plant seeds, and transgenic propagation material, with modified 5-aminolevulinic acid biosynthesis containing one or more functionally active nucleic acid molecules encoding a protein with the function of an ALAS, preferably a feedback-regulated ALAS, especially preferably purple bacteria ALAS, active fragments thereof or an antisense or complementary sequence thereof, which are stably integrated into the plant genome by a method known per se for the production of transgenic plant cells or plants, plant parts, plant seeds or propagation material wherein the transgenic plant is monocotyledonous plant, preferably a maize plant.

The invention furthermore relates to the use of at least one nucleic acid molecule (NA) encoding a protein with the function of an ALAS selected from the group of the feedback-regulated ALASs, animal ALASs and bacterial ALASs, preferably a feedback-regulated ALAS, especially preferably purple bacteria ALAS, an active fragment thereof or an antisense or complementary sequence thereof for producing transgenic plant cells or plants with modified 5-aminolevulinic acid biosynthesis, preferably for expressing a protein with the function of an ALAS according to the invention or of an active fragment thereof in transgenic plant cells or plants, or else preferably for producing transgenic plant cells or plants whose expression of a protein with the function of a GSAAT or an active fragment thereof is suppressed or inhibited.

The invention furthermore relates to the use of at least one nucleic acid molecule (NA) encoding a protein with the function of an ALAS, preferably a feedback-regulated ALAS, especially preferably a purple bacteria ALAS, an active fragment thereof or an antisense or complementary sequence thereof for producing transgenic plant cells or plants with modified 5-aminolevulinic acid biosynthesis, preferably for expressing a protein with the function of an ALAS according to the invention or an active fragment thereof in transgenic plant cells or plants or else preferably for producing transgenic plant cells or plants, whose expression of a protein with the function of a GSAAT or an active fragment thereof is suppressed or inhibited, wherein the transgenic plant is a monocotyledonous plant, preferably a maize plant.

A variety of genes which are known from the literature and which encode proteins with ALAS activity can be employed for the production of transgenic plants which are capable of producing ALA by means of the Shemin metabolic pathway.

Thus, suitable nucleic acid sequences encoding proteins with ALAS activity are those which are derived from amino acid sequences of proteins with ALAS activity or their genes, for example from animals and bacteria, or, generally, from feedback-regulated ALAS from prokaryotic or eukaryotic organisms or their active fragments, for example the ALAS from the purple bacteria of thealpha group such as *Rhodobacter sphaeroides*, SEQ ID NO: 1 or SEQ ID NO: 2 (Neidle & Kaplan (1993) Journal of Bacteriology 175: 2292–2303) or *Rhodobacter capsulatus*, SEQ ID NO: 3 (Hornberger et al. (1990) Mol. Gen. Genet. 221: 371–378).

A balanced ALA synthesis can be ensured, for example, in the following manner, so that the term feedback-regulated in context with the biological ALAS activity is to be understood as illustrated hereinbelow:

Firstly, nucleic acids (NA) encoding proteiris with ALAS activity and which exhibit a pronounced feedback regulation by heme can be employed for transforming plants. Besides chlorophyll, heme is an important product formed from ALA. The heme synthesis rate, like the synthesis of all the other tetrapyrroles, is coupled to the supply of ALA and thus reflects the synthetic capacity for the intermediate ALA and thus indirectly also the possible substrate flux into chlorophyll biosynthesis. Nonexclusive examples which are suitable for the heterologous expression of feedback-regulated enzymes with ALAS activity in plants are therefore ALAS-encoding NAs from *Rhodobacter sphaeroides, Rhodobacter capsulatus* and other purple bacterias from the alpha group.

In plant cells, the feedback regulation of the enzymatic activity of a heterologous ALAS can take place, for example, in plastids and in the mitochondria since the regulatorily active compounds, for example heme, are formed in these organelles starting from 5-aminolevulinate (ALA). It is therefore particularly advantageous to express a heterologous NA encoding a feedback-regulated protein with ALAS activity in such a way that the functionally intact expression products (ALAS) are present in the plastids or mitochondria.

ALA synthesized in mitochondria can be exported into the plastids, where the enzymes of the subsequent tetrapyrrole biosynthesis are localized, by means of the transport systems which exist in the plant.

The localization of an ALAS in plastids can be achieved, for example, by inserting, by means of methods known to the skilled worker, an NA encoding a protein with ALAS activity into the plastome of a plant under the control of a promoter which is active in plastids. Promoters which are available for this purpose are all promoters which are constitutively active in plastids, preferably for example the expression signal sequences of the psbA cassette (Staub & Maliga (1993) EMBO Journal 12: 601–606; Zoubenko et al. (1994) Nucleic Acids Research 22: 3819–3824) and the Prrn promoter (Svab & Maliga (1993) Proc. Natl. Acad. Sci. USA 90: 913–917).

The promoters can be inserted into the plastome for example by known methods together with the heterologous NA encoding a protein with the function of an ALAS, or the heterologous NA is inserted into the plastome in such a way that it is under the control of an already existing promoter (Staub & Maliga (1995) Plant Journal 7: 845–848).

Moreover, localization of an ALAS in the plastid may also be achieved by first synthesizing the ALAS in the cytoplasm together with a suitable plastid targeting sequence (transit peptide) and importing it into the plastid during or after its synthesis. To this end, the skilled worker has available to him a large number of promoters, plastid targeting sequences and fusion strategies for NAs encoding a targeting sequence and NAs encoding a protein with ALAS activity.

Promoters which can be employed for the purposes of the present invention are all those which are capable of causing, in plants, the transcription of DNA sequences. Such promoters are preferably derived from the genome of plants or plant-pathogenic viruses, for example the CaMV35S promoter and its derivatives, preferably from the plastome, but equally preferably from nuclear DNA, especially preferably from the plastome of plants. The promoter employed must allow a sufficient expression level of the ALAS gene as to impart, to the transgenic plant, a resistance to inhibitors of the C5 biosynthetic pathway for ALA.

The NA encoding a protein with ALAS activity is cloned, preferably under the control of a promoter, as a fusion with a DNA sequence encoding a plastic transit peptide so that the primary translation product is provided N-terminally with a plastid transit peptide and is imported into plastids. Plastid transit peptides which are preferably used are those peptide sequences which, as N-terminal fusion, cause the translocation of polypeptide chains from the cytoplasm into plastids and which are eliminated during or after this process. An especially preferred transit peptide for proteins with ALAS activity which may be mentioned is the ribulosebisphosphate carboxylase small subunit transit peptide.

The localization of an ALAS according to the invention in mitochondria can be achieved by first synthesizing the protein in the cytoplasm with a suitable mitochondrial targeting sequence and importing it into the mitochondrium during or after its synthesis. To this end the skilled worker also has available to him a large number of promoters, mitochondrial targeting sequences and fusion strategies for sequences encoding a targeting sequence and sequences encoding a protein with ALAS activity.

For the purposes of the present invention, the same promoters may be used as have been described for the localization of the expression products in the plastid.

The NA encoding a protein with ALAS activity is preferably cloned under the control of a promoter as fusion with a DNA sequence encoding a mitochondrial transit peptide so that the primary translation product is provided N-terminally with a mitochondrial transit peptide and imported into mitochondria.

Mitochondrial transit peptides which are preferably used are those peptide sequences which, as N-terminal fusion, cause the translocation of polypeptide chains from the cytoplasm into mitochondria and which are eliminated during or after this process.

A further subject of the invention is therefore a method for producing transgenic plants, transgenic plant cells, transgenic plant parts, transgenic plant seeds, and transgenic propagation material, with modified 5-aminolevulinic acid biosynthesis containing one or more functionally active nucleic acid molecules encoding a protein with the function of an ALAS selected from the group of the feedback-regulated ALASs, animal ALASs and bacterial ALASs, preferably a feedback-regulated ALAS, especially preferably purple bacteria ALAS, active fragments thereof or an antisense or complementary sequence thereof, where said nucleic acid molecules are under the control of a feedback-regulated promoter, and the use of a feedback-regulated promoter, preferably of a promoter of a plant GSAAT or glutamyl-tRNA reductase, in a method according to the invention for the production of transgenic plant cells or plants with modified 5-aminolevulinic acid biosynthesis.

The invention also relates to a method for producing transgenic plants, transgenic plant cells, transgenic plant parts, transgenic plant seeds, and transgenic propagation material, with modified 5-aminolevulinic acid biosynthesis containing one or more functionally active nucleic acid molecules encoding a protein with the function of an ALAS, preferably a feedback-regulated ALAS, especially preferably purple bacteria ALAS, active fragments thereof or an antisense or complementary sequence thereof, where said nucleic acid molecules are under the control of a feedback-regulated promoter, and the use of a feedback-regulated promoter, preferably of a promoter of a plant GSAAT or glutamyl-tRNA reductase, in a method according to the invention for the production of transgenic plant cells or plants with modified 5-aminolevulinic acid biosynthesis, wherein the transgenic plant is a monocotyledonous plant, preferably a maize plant.

On the other side, it is especially advantageous to clone the ALAS according to the invention under the control of a promoter which is regulated specifically in plants, so as to achieve directed, feedback-regulated expression. Suitable for this purpose are, for example, the promoters of the enzymes of plant porphyrin biosynthesis, preferably the promoters of the genes encoding glutamyl-tRNA reductase and GSAAT, for example by using promoter sequences located in the region of approx. 2 kb (kilobases) long nucleic acid sections of the encoding regions of said genes which are located upstream (in 3'-direction). Being under the control of one of these promoters allows the NA encoding a heterologous protein with ALAS activity and the plant genes encoding glutamyl-tRNA reductase and GSAAT to be expressed only when physiological demand for ALA exists.

Moreover, the combined use of an NA encoding an ALAS which is feedback-regulated at protein and gene expression level is also particularly advantageous, i.e. to express both an ALAS protein which has a feedback-regulated enzymatic activity and to place the gene expression of the feedback-regulated ALAS under the control of a feedback-regulated promoter.

NAs encoding proteins with ALAS activity can be isolated from animal, fungal or suitable bacterial organisms or produced synthetically. The nucleic acid molecules will preferably be cloned by means of customary methods of molecular biology (Ausubel et al. in "Current Protocols in Molecular Biology", John Wiley & Sons Inc., ISBN 0471–50338-X) starting from DNA or RNA from the donor organism in question. The sequence of the NAs can also be modified, truncated or extended in a multiplicity of manners using customary methods of molecular biology so that derivatization, for example by mutation, deletion, substitution or insertion can be effected.

The invention also relates to non-naturally occurring chimeric genes comprising at least one promoter which is suitable for expressing an ALAS according to the invention in plants and which is functionally fused to a DNA molecule encoding a protein with the function of an ALAS or an active fragment thereof or an antisense or complementary sequence thereof.

The invention also relates to recombinant vectors, in particular to plasmids, cosmids, viruses and other vectors conventionally used in genetic engineering, comprising at least one non-naturally occurring chimeric gene according to the invention.

In a preferred embodiment, nucleic acid molecules contained in the vectors are linked to regulatory elements which ensure the transcription and synthesis of a translatable RNA in plant cells.

The invention also relates to transgenic plant cells which are transformed and/or genetically modified with a DNA molecule encoding a protein with the function of an ALAS according to the invention or an active fragment thereof or an antisense or complementary sequence thereof or a chimeric gene or vector according to the invention, and to cells which are derived from such transformed and/or modified cells which contain a nucleic acid molecule to be used in accordance with the invention or a gene or vector according to the invention.

The invention also relates to transgenic plant cells which are transformed and/or genetically modified with a DNA molecule encoding a protein with the function of an ALAS or an active fragment thereof or an antisense or complementary sequence thereof or a chimeric gene or vector according to the invention, and to cells which are derived from such transformed and/or modified cells which contain a nucleic acid molecule to be used in accordance with the invention or a gene or vector according to the invention, wherein the transgenic plant is a monocotyledonous plant, preferably a maize plant.

The invention also relates to transgenic plants, transgenic plant cells, transgenic plant parts, transgenic plant seeds, and transgenic propagation material, which can be produced, i.e. which are obtainable, preferably obtained, by a method according to the invention, containing a DNA molecule encoding a protein with the function of an ALAS selected from the group of the feedback-regulated ALASs, animal ALASs and bacterial ALASs, or an active fragment thereof or an antisense or complimentary sequence thereof, in particular useful plants or ornamentals.

The invention also relates to transgenic plants, transgenic plant cells, transgenic plant parts, transgenic plant seeds, and transgenic propagation material, which can be produced, i.e. which are obtainable, preferably obtained, by a method according to the invention, containing a DNA molecule encoding a protein with the function of an ALAS or an active fragment thereof or an antisense or complimentary sequence thereof, in particular useful plants or ornamentals, wherein the transgenic plant is a monocotyledonous plant, preferably a maize plant.

Such plant cells comprise one or more nucleic acid molecule(s) to be used in accordance with the invention, this (these) nucleic acid molecule(s) preferably being linked to regulatory DNA elements which ensure transcription in plant cells, in particular to a promoter.

Such cells can be distinguished from naturally occurring plant cells by the fact that they contain at least one chimeric gene according to the invention which does not occur naturally in these cells, or by the fact that such a molecule exists integrated at a site in the cell's genome where it does not occur naturally, i.e. in a different genomic environment.

To transform plants, suitable NA constructs are produced which contain a translatable sequence in coding a protein with ALAS activity.

A wide range of techniques is available to the skilled worker in plant biotechnology in order to produce suitable DNA constructs for expressing a heterologous gene in plants and transform plants with this DNA construct. Such DNA constructs are preferably produced by cloning a DNA sequence encoding ALAS under the control of a plant promoter in a plant transformation vector. Especially preferably suitable for this purpose are binary plant transformation vectors such as, for example, PBIB or pPCV801 and their derivatives.

The gene encoding a protein with ALAS activity can also be inserted into the plant genome without a DNA sequence encoding an N-terminal plastid or mitochondrial targeting peptide under the control of a promoter which is active in plants, so that the primary translation product is expressed directly in the cytoplasm to give the active protein.

Plant cells or plastids are transformed with one of the above-described DNA constructs which is suitable for functionally expressing a gene encoding a protein with ALAS activity in plants. Preferably, one of the current genetic engineering methods for transforming plants (for example Potrykus & Spangenberg (Eds.) "Gene Transfer to Plants" (1995) Springer-Verlag ISBN 3-540 58406-4) or plastids (for example Zoubenko et al. (1994) Nucleic Acids Research 22: 3819–1824) is employed for this purpose.

The invention therefore also relates to a method for producing transgenic plants, transgenic plant cells, transgenic plant parts, transgenic plant seeds, and transgenic propagation material with modified 5-aminolevulinic acid biosynthesis containing one or more functionally active nucleic acid molecules encoding a protein with the function of an ALAS selected from the group of the feedback-regulated ALASs, animal ALASs and bacterial ALASs, preferably of a feedback-regulated ALAS, especially preferably purple bacteria ALAS, active fragments thereof or an antisense or complementary sequence thereof, where said nucleic acid molecules are stably integrated into the plant plastome by means of plastid transformation.

The invention therefore also relates to a method for producing transgenic plants, transgenic plant cells, transgenic plant parts, transgenic plant seeds, and transgenic propagation material with modified 5-aminolevulinic acid biosynthesis containing one or more functionally active nucleic acid molecules encoding a protein with the function of an ALAS, especially preferably purple bacteria ALAS, active fragments thereof or an antisense or complementary sequence thereof, where said nucleic acid molecules are stably integrated into the plant plastome by means of plastid transformation, wherein the transgenic plant is a monocotyledonous plant, preferably a maize plant.

Suitable recipient plants for a heterologous gene encoding a protein with ALAS activity are all agriculturally important monocotyledonous and dicotyledonous, preferably monocotyledonous, crop plants in which herbicidal inhibitors of the C5 metabolic pathway can be employed for controlling undesirable accompanying vegetation, preferably maize and other cereals such as, for example, wheat, rye, barley, panic grasses and rice, and also cotton, tobacco, sugar beet, sugar cane, potatoes, oil seed rape, sunflowers, soybeans, vegetables and fruit.

When expressing the nucleic acid molecules to be used in accordance with the invention in plants, it is possible, in principle, for the protein synthesized to be localized in any compartment of the plant cell. To achieve localization in a particular compartment, the encoding region may, if appropriate, be linked to DNA sequences which ensure localization in the compartment in question. Such sequences are known (see, for example, Braun et al., EMBO J. 11 (1992), 3219–3227; Wolter et al., Proc. Natl. Acad. Sci. USA 85 (1988), 846–850; Sonnewald et al., Plant J.1 (1991), 95–106).

The transgenic plant cells can be regenerated to give rise to entire plants by techniques known to the skilled worker. The plants obtained by regeneration of the transgenic plant cells according to the invention are also subject matter of the present invention. Plants which comprise the above-described transgenic plant cells are also subject matter of the invention. In principle, the transgenic plants can be plants of any plant species, i.e. not only monocotyledonous, but also dicotyledonous plants.

They are preferably useful plants or ornamentals such as, for example, cereal species (rye, barley, oats, wheat, rice, maize), fruit and vegetable species, casava, potatoes, soybeans, sugar beet and the like.

The invention also relates to propagation material of the plants according to the invention, for example to fruits, seeds, tubers, root stocks, seedlings and cuttings.

To express the nucleic acid molecules to be used in accordance with the invention in plant cells in sense orientation, they are linked to regulatory DNA elements which ensure transcription in plant cells. These include, in particular, promoters. In general, any promoter which is active in plant cells is suitable for expression.

The promoter may be chosen in such a way that expression is constitutive or only takes place in a certain tissue, at a certain point in time of the plant's development or at a point in time determined by external factors. As regards the plant, the promoter can be homologous or heterologous. Examples of suitable promoters are the cauliflower mosaic virus 35S RNA promoter and the maize ubiquitin promoter for constitutive expression, the patatin gene promoter B33 (Rocha-Sosa et al., EMBO J. 8 (1989), 23–29) for sink-specific expression (for example potato tubers, beet, tomato fruit) or a promoter which ensures expression only in photosynthetically active tissues, for example the ST-LS1 promoter (Stockhaus et al., Proc. Natl. Acad. Sci. USA 84 (1987), 7943–7947; Stockhaus et al., EMBO J. 8 (1989), 2445–2451), all promoters which are constitutively active in plastids, for example the psbA cassette expression signal sequences (Staub & Maliga (1993) EMBO Journal 12: 601–606; Zoubenko et al. (1994) Nucleic Acids Research 22: 3819–3824) and the Prrn promoter (Svab & Maliga (1993) Proc. Natl. Acad. Sci. USA 90: 913–917), or, for endosperm-specific expression, the wheat HMG promoter, the USP promoter, the phaseolin promoter, or promoters from maize zein genes. Furthermore, a termination sequence may be present which serves for correctly terminating transcription and for adding a poly-A tail to the transcript, which is assumed to have a function in stabilizing the transcripts. Such elements are described in the literature (Gielen et al., EMBO J. 8 (1989), 23–29) and are, in general, exchangeable as desired.

A large number of cloning vectors are available for preparing the introduction of foreign genes into higher plants, these cloning vectors containing a replication signal for *E. coli* and a marker gene for the selection of transformed bacterial cells. Examples of such vectors are pBR322, pUC series, M13mp series and pACYC184. The desired sequence can be introduced into the vector at a suitable restriction cleavage site. The plasmid obtained is used for transforming *E. coli* cells. Transformed *E. coli* cells are grown in a suitable medium and then harvested and lysed. The plasmid is recovered. Analytical methods for characterizing the plasmid DNA obtained are, in general, restriction analyses, gel electrophoreses and other methods of biochemistry and molecular biology. After each manipulation, the plasmid DNA can be cleaved and DNA fragments obtained can be linked to other DNA sequences. Each plasmid DNA sequence can be cloned in the same or other plasmids.

A large number of techniques is available for introducing DNA into a plant host cell. These techniques encompass the transformation of plant cells with T-DNA using *Agrobacterium tumefaciens* or *Agrobacterium rhizogenes* as transformation agent, protoplast fusion, injection, DNA electroporation, the introduction of DNA by means of the biolistic method and the like.

When injecting and electroporating DNA into plant cells, the plasmids used need not meet any particular requirements. Simple plasmid such as, for example, pUC derivatives, may be used. If, however, whole plants are to be regenerated from such transformed cells, the presence of a selectable marker gene is required.

Depending on the method by which the desired genes are introduced into the plant cell, other DNA sequences may be required. If, for example, the Ti or Ri plasmid is used for transforming the plant cell, at least the right and left border, but frequently the right and left border of the Ti and Ri plasmid T-DNA must be linked as flanking region with the genes to be introduced.

If agrobacteria are used for the transformation, the DNA to be introduced must be cloned into specific plasmids; viz either into an intermediary vector or into a binary vector. The intermediary vectors can be integrated by homologous recombination into the Ti or Ri plasmid of the agrobacteria due to sequences which are homologous to sequences in the T-DNA. The Ti or Ri plasmid also contains the vir region which is required for transferring the T-DNA. Intermediary vectors cannot replicate in agrobacteria. The intermediary vector can be transferred to *Agrobacterium tumefaciens* by means of a helper plasmid (conjugation). Binary vectors are capable of replication both in *E. coli* and in agrobacteria. They contain a selection marker gene and a linker or polylinker which is framed by the left and right T-DNA border region. They can be transformed directly into the agrobacteria (Holsters et al. Mol. Gen. Genet. 163 (1978), 181–187). The agrobacterium which acts as the host cell should contain a plasmid which carries a vir region. The vir region is required for transferring the T-DNA into the plant cell; additional T-DNA may be present. This transformed agrobacterium is used for transforming plant cells.

The use of T-DNA for transforming plant cells is described extensively in EP 120 516; Hoekema, In: The Binary Plant Vector System Offsetdrukkerij Kanters B. V., Alblasserdam (1985), Chapter V; Fraley et al., Crit. Rev. Plant Sci., 4, 1–46 and An et al. EMBO J. 4 (1985), 277–287.

To transfer the DNA into the plant cell, plant explants may advantageously be cocultured with *Agrobacterium tumefaciens* or *Agrobacterium rhizogenes*. Whole plants may again be regenerated from the infected plant material (for example leaf sections, stalk sections, roots, but also protoplasts or suspension-cultured plant cells) in a suitable medium which may contain antibiotics or biocides for selecting transformed cells. The resulting plants can then be tested for the presence of the DNA which has been introduced. Other possibilities of introducing foreign DNA with the biolistic method or by protoplast transformation are known (cf., for example, Willmitzer, L., 1993 Transgenic plants. In: Biotechnology, A Multi-Volume Comprehensive Treatise (H. J. Rehm, G. Reed, A. Pühler, P. Stadler, eds.), Vol. 2, 627–659, VCH Weinheim).

Alternative systems for the transformation of monocotyledonous plants are the transformation by means of the biolistic approach, the electrically or chemically induced DNA uptake into protoplasts, the electroporation of partially permeabilized cells, the macroinjection of DNA into influorescences, the microinjection of DNA into microspores and proembryos, the DNA uptake by germinating pollen, and the DNA uptake in embryos by swelling (review: Potrykus, Physiol. Plant (1990), 269–273).

While the transformation of dicotyledonous plants via Ti plasmid vector systems with the aid of *Agrobacterium tumefaciens* is well established, later publications suggest that even monocotyledonous plants are indeed accessible to transformation by means of Agrobacterium-based vectors (Chan. et al., Plant Mol. Biol. 22 (1993), 491–506; Hiei et al., Plant J. 6 (1994), 271–282, Bytebier et al., Proc. Natl. Acad. Sci. USA 84 (1987), 5345–5349; Raineri et al., Bio/Technology 8 (1990), 33–38; Gould et al., Plant Physiol. 95 (1991), 426–34; Mooney et al., Plant Cell Tiss. & Org. Cult. 25 (1991), 209–218; Li et al., Plant Mol. Biol. 20 (1992), 1037–1048).

Three of the abovementioned transformation systems were established in the past for a variety of cereals: the electroporation of tissue, the transformation of protoplasts, and the DNA transfer by particle bombardment of regenerable tissue and cells (Jathne et al., Euphytica 85 (1995), 3544).

The transformation of wheat is described in various references (review: Maheshwari et al., Critical Reviews in Plant Science 14 (2) (1995), 149–178), cf. also Hess et al., (Plant Sci. 72 (1990), 233), Vasil et al. (Bio/Technology 10 (1992), 667–674), Weeks et al. (Plant Physiol. 102 (1993), 1077–1084) and Becker et al. (Plant J. 5(2) (1994), 299–307).

Once the DNA introduced is integrated into the genome of the plant cell, it is, as a rule, stable and is retained in the progeny of the originally transformed cell. It normally contains a selection marker which mediates resistance to a biocide such as phosphinothricin or an antibiotic such as kanamycin, G 418, bleomycin or hygromycin and the like to the transformed plant cells. The marker, which is chosen individually, should therefore allow the selection of transformed cells over cells which lack the DNA introduced. Transformed cells according to the invention inherently comprise a marker over GSAAT inhibitors.

The transformed cells grow within the plant in the customary manner (see also McCormick et al., Plant Cell Reports 5 (1986), 81–84). The resulting plants can be grown normally and hybridized with plants which have the same transformed genetic material, or other genetic material. The resulting hybrids have the corresponding phenotypic characteristics. Seeds may be obtained by the plant cells.

Two or more generations should be grown in order to ensure that the phenotypic trait is stably retained and inherited. Also, seeds should be harvested to ensure that the relevant phenotype, or other characteristics, have been retained.

The transgenic plants according to the invention can be exploited in practice in conjunction with the herbicides whose mechanism of action is based, at least to some extent, on an inhibition of GSAAT and thus of the C5 pathway.

The invention therefore also relates to a method for controlling undesired vegetation in crops of useful plants, which comprises employing a useful plant which exhibits one or more nucleic acid molecules encoding for a protein of an ALAS according to the invention and apply, to the location of this plant, to the plant itself or to its propagation material, a herbicidal agent whose mechanism of action is based at least partially on a, preferably specific, inhibition of GSAAT.

The rational development of such herbicides is also subject matter of the invention.

It has been found that herbicidal inhibitors of the plant C5 pathway can be found when the effect of a chemical compounds on the activity of plant GSAAT is determined and chemically diverse compounds are screened in individual or serial studies. Automation of a suitable GSAAT activity test thus allows a large number of compounds to be studied in this manner and allows the method to be suitable for practice conditions.

The invention therefore also relates to a preferably automated method for determining the effect of a test substance on an GSAAT activity, where
  a) the enzymatic GSAAT activity is determined in-the absence of a test substance;
  b) the enzymatic GSAAT activity is determined in the presence of a testsubstance; and
  c) the enzymatic activities determined under a) and b) are compared.

The method is suitable for finding specific inhibitors or activators (i.e. effectors) of the enzymatic GSAAT activity so that, inter alia, substances can be identified which have a potential herbicidal or growth-inhibitory, but also growth-promoting, action. The chemical compound to be tested is employed preferably in concentrations between $10^{-9}$ M and $10^{-3}$ M, especially preferably in concentrations between $10^{-7}$ M and $10^{-4}$ M.

The enzyme inhibition or enzyme activation (i.e. of the effector efficiency) can be quantified by simply comparing the catalytic GSAAT activity in the absence and in the presence of the test substance to be examined in a manner known to the skilled worker under test conditions which are otherwise identical.

To determine the GSAAT activity, various biochemical measurement methods can be employed by which either the formation of the reaction products of the GSAAT-catalyzed reaction, for example ALA, or else a decrease in the concentration of the enzyme substrates such as glutamate semialdehyde, are measured, for example by an end-point determination or after enzymatic conversion of the substrate which, if appropriate, had been radiolabeled or provided with other customary markers, or by subsequent reactions, for example by coupled enzymatic reactions.

A large number of standard methods for determining enzyme activities are available to the skilled worker who is familiar with carrying out enzyme tests (see, for example, Bergmeyer, H. U., Methoden der enzymatischen Analyse [Methods of Enzymatic Analysis], Vols. 1 and 2, Verlag Chemie, Weinheim (1974), Suelter, C. H., Experimentelle Enzymologie: Grundlagen für die Laborpraxis [Experimental Enzymology: Basics for Laboratory Practice], Fischer Stuttgart (1990)).

The methods according to the invention for determining the effector efficiency of test substances can be carried out on purified GSAAT, or else using entire cells of a recombinant organism which recombinantly expresses GSAAT, on GSAAT-containing extracts of this organism or enriched GSAAT-containing fractions of this organism. Bacterial, insect and yeast cells are mentioned as preferred recombinant host organism. Alternatively, a GSAAT isolated from plant tissue or plant cell cultures may also be used.

The invention therefore also relates to the use of a method according to the invention and to the use of a protein, preferably a recombinant protein, with the function of a GSAAT for identifying GSAAT effectors, preferably in an automated method, for example in a high-throughput screening, the procedure of which requires that the method for determining the enzyme activity is capable of being automated.

Effectors according to the invention, or effectors which have been identified in accordance with the invention, preferably inhibitors, affect (inhibit) the activity of the enzyme, preferably under the test conditions described, preferably by at least 30% especially preferably by at least 50%.

The invention therefore furthermore relates to effectors, i.e. activators or inhibitors of the enzymatic GSAAT activity which can be identified by means of the methods according to the invention, in particular pesticidally or herbicidally active effectors of plant GSAAT, specifically structural analogs of glutamate semialdehyde, glutamate or 5-aminolevulinate, and their use as pesticides or herbicides.

Besides 3-amino-2,3-dihydrobenzoic acid, only extremely non-selective GSAAT inhibitors such as, for example, amino oxyacetic acid, have been known to date. The known inhibitors cannot be employed as herbicides since they are highly toxic not only to plants. Only the development of specific inhibitors of the plant C5 metabolic pathway for 5-aminolevulinic acid, which can be employed as herbicides in agriculture, suggests that the production of transgenic crop plants which are resistant to inhibitors of the C5 pathway is advantageous and makes economic sense.

A series of suitable methods are available for determining the enzymatic GSAAT activity where a GSAAT is incubated with a suitable substrate such as, for example, glutamate-1-semialdehyde (GSA) in a suitable reaction buffer under suitable reaction conditions with regard to reaction temperature and pH. Plant GSAAT is preferably used for identifying effective enzyme inhibitors, especially preferably the *Arabidopsis thaliana* GSAAT (SEQ ID NO: 5) or the Hordeum vulgare GSAAT (SEQ ID NO: 6). The GSAAT can either be isolated from the plants in question in a manner known to the skilled worker or else produced by recombinant technology in transgenic host cells starting from cDNA which is known from the literature.

Other compounds such as, for example, 4,5-diaminovaleric acid, 4,5-dioxovaleric acid and, in particular, mixtures of these compounds can be used as substrates instead of glutamate-1-semialdehyde. The enzymatic reaction can be influenced by adding pyridoxal phosphate or pyridoxamine phosphate.

A particularly suitable example of an embodiment of the GSAAT activity test is shown hereinbelow, and this is also especially suitable for an automated procedure of the GSAAT test:

Glutamate-1-semialdehyde can be reacted in a reaction buffer in the pH range of pH 6 to pH 8 by an enzyme with GSAAT activity to give 5-aminolevulinic acid. The 5-aminolevulinic acid can then be detected by means of two derivatization steps. First, a compound of the formula R—CO—CH$_2$—CO—R' such as, for example, acetylacetone, acetoacetic acid, amides and salts of acetoacetic acid, acetoacetic esters (methyl ester, ethyl ester, isopropyl ester and the like) or derivatives of these compounds is added to the solution in at least a ten-fold molar excess over the expected amount of 5-aminolevulinic acid. The mixture is then heated, for example for a few minutes (80° C. to boiling point of the mixture) or incubated for 15 minutes or longer at 12° C. to 80° C. During this incubation time, a condensation reaction takes place between the aminolevulinic acid and the added compound with formation of a pyrrole derivative. Then, the concentration of the pyrrole derivative is determined for example by adding Ehrlich's reagent (for example 1 volume). In this detection method, the pyrrole derivative together with the 4-diaminobenzaldehyde in Ehrlich's reagent forms a colored complex whose concentration can be determined photometrically via absorption measurement. A suitable wavelength for determining the absorption is, for example, between 530 and 550 nm. The amount of 5-aminolevulinic acid which has been formed enzymatically can be calculated with the aid of a calibration series with 5-aminolevulinic acid solutions of known concentrations which are derivatized in the same manner.

The suitable compositions of the reagents or the concentrations of salts, substrates and proteins, the pH values, the temperatures, the batch volumes and the wavelengths for measurement or detection can vary within wide limits.

A GSAAT activity test allows the skilled worker to determine the effectory, i.e. activatory or inhibitory, properties of chemical compounds on GAAAT activity in a varied, known manner.

Varied methods are available to the skilled worker for checking the action of a GSAAT inhibitor on plants in vivo. The substances to be studied (for example defined chemical compounds, but also heterogeneous mixtures of materials)

are applied to plants, it being possible to use a wide range of auxiliaries such as, for example, wetters or solvents. After application of the substances to be studied, the plants are scored. Substances which damage a plant by selective inhibition of GSAAT or of the C5 metabolic pathway cause at least one characteristic symptom. Chloroses which may be especially pronounced in newly-formed tissue and which can turn to necroses, for example when exposed to light, are frequently formed after application. Other symptoms may be growth depression or else very rapid dying of the plant. Depending on the plant species, the symptoms differ as a function of their different sensitivities and as a function of the inhibitor's properties.

A simple possibility for an in-vivo test which is suitable for practice conditions is the Lemna test described in Example 8.

The combination of the in-vitro enzyme test according to the invention with an in-vivo test, preferably a Lemna test, especially preferably essentially under the conditions mentioned in Example 8, the concentration range of the test substance preferably being in the range of $10^{-6}$ to $10^{-4}$, constitutes a rational method for the development of herbicides whose action is based on an inhibition of plant GSAAT.

The invention therefore also relates to a method for finding herbicidally active substances, which comprises testing the test substance to be studied as described above for an effector efficiency on GSAAT and preferably also subjecting it to a Lemna test.

The invention relates to the use as herbicide of a compound which in the described test methods for effector properties on GSAAT exhibits an at least 30%, preferably at least 50%, inhibitor action and is preferably active in the Lemna test.

Active preferably means the appearance of chlorotic tissue, especially preferably the appearance of chlorotic tissue and growth depression of the plant, preferably within ten, especially preferably within seven, days.

The invention also relates to a method for controlling undesired vegetation in crops of useful plants, which comprises applying, to the location of the useful plant, the useful plant or its propagation material, a herbicidal composition comprising a compound which, in the described above test method, in a molar concentration range of $10^{-7}$ to $10^{-4}$ exhibits an at least 30%, preferably at least 50%, inhibitor action on GSAAT and which is preferably active in the Lemna test.

The useful plants are preferably transgenic plants according to the invention with a modified 5-levulinic acid biosynthesis.

The contents of german patent application 197 54 929.2, whose priority is claimed in the present application, and the summary of that application are herewith expressly referred to; they are incorporated into the present description by reference:

The examples which follow are intended to illustrate the invention in greater detail without constituting any form of limitation.

EXAMPLE 1

Construction of a Transformation Vector for Transferring an ALAS Gene to Plants

The *Rhodobacter sphaeroides* hemA gene encoding an ALAS was isolated for the purpose of expressing it in plants. To this end, the oligodeoxynucleotides ALAS1 and ALAS2 were constructed. ALAS1 has the sequence 5'-gactgtgcatgcaggactacaatctggcactc-3', (SEQ ID NO: 9), has an SphI restriction cleavage site at the 5' end and is derived in the 3' region from positions 1950 to 1967 of the gene bank entry L07490 (SEQ ID NO: 1). ALAS2 has the sequence 5'-ctgactctgcagtcaggcaacgacctcggc-3', has a PstI restriction cleavage site at the 5' end and is derived in the 3' region from positions 3170 to 3153 of the gene bank entry L07490.

To amplify the *Rhodobacter sphaeroides* hemA gene fragment which corresponds to positions 1950 to 3170 of the gene bank entry L07490, a polymerase chain reaction (PCR) was carried out. For the PCR mixture, 5 $\mu$l of a 1:10 dilution in water of a stationary culture of *Rhodobacter sphaeroides* strain ATCC #35054 (cultured as specified in the American Type Culture Collection catalog, Manassas, Va. 20110-2209, USA), in each case 10 nmol of dATP, dCTP, dGTP and dTTP and in each case 25 pmol of primer ALAS1 and ALAS2 were mixed in a total volume of 50 $\mu$l, $^1/_{10}$ volume of 10×Taq buffer (100 mM Tris/HCl pH 9.0, 500 mM KCl, 15 mM MgCl$_2$, 0.1% gelatin and 1% Triton X-100) was added to the reaction mixture. The mixtures were covered with 3 drops of liquid paraffin and subsequently heated in the PCR apparatus to 94° C. After incubation for 2 minutes, 2.5 u taq DNA polymerase were added. The PCR was carried out in successive thermocycles consisting of the three steps which follow: 1. denaturation of the duplex DNA at 96° C. for 1 minute; 2. annealing of the primers to the template DNA at 50° C. for 1 minute; 3. DNA synthesis at 72° C. for 3 minutes. This cycle was carried out 30 times in succession. Then, the mixture was incubated for 5 minutes at 60° C. The 1247 $\mu$bp reaction product was isolated by preparative agarose gel electrophoresis and subsequently cleaved with the restriction enzymes SphI and PstI for subsequent cloning.

For cloning, the vector pGEM3Zf-(Promega) was cleaved with SphI and PstI, and the approx. 3100 bp vector fragment was isolated. The SphI/PstI vector fragment was ligated with the 1235 SphI/PstI fragment of the hemA PCR product. *Escherichia coli* XL-1 Blue (Stratagene) was transformed with the ligation product.

The sequence of the hemA PCR product, cloned in pGEM3Zf-, in the resulting plasmid pALAS1 is identical with the consensus of several other independent plasmid clones and is shown in SEQ ID NO: 7 (without cloning cleavage sites).

The 1235 b SphI/PstI fragment from pALAS1 was ligated with the 222 bp PstI(2335)/HindIII(2557) fragment from p35StpASN and the 3438 bp HindIII(2557)/SphI(1199) fragment from p35StpASNT. The plasmid map of vector vector p35StpANS is depicted in FIG. 1

Key to FIG. 1: The vector pStpASN is derived from pUC18 (amp=beta-lactamase) and contains a cassette with the following elements: 35S promoter=CaMV35S promoter, tp'-'tp'-'tp'=modified chloroplast targeting sequence of the pea ribulosebisphosphate carboxylase small subunit, 35S terminator=CaMV35S transcription terminator).

The ligation product of the three fragments was termed pALAS2. In this construct, the sequence encoding for *Rhodobacter sphaeroides* ALAS is fused in the reading frame at the 5' end via the SphI cleavage site with a sequence encoding a modified chloroplast targeting sequence. This sequence is derived from the chloroplast targeting sequence of the pea ribulosebisphosphatecarboxylase small subunit and contains an internal sequence duplication corresponding to positions 985 to 1041 in p35StpASN, which are repeated as positions 1045 to 1101 in p35StpASN. Transcription of the fused gene is regulated by the CaMV35S promoter.

Figure 2:
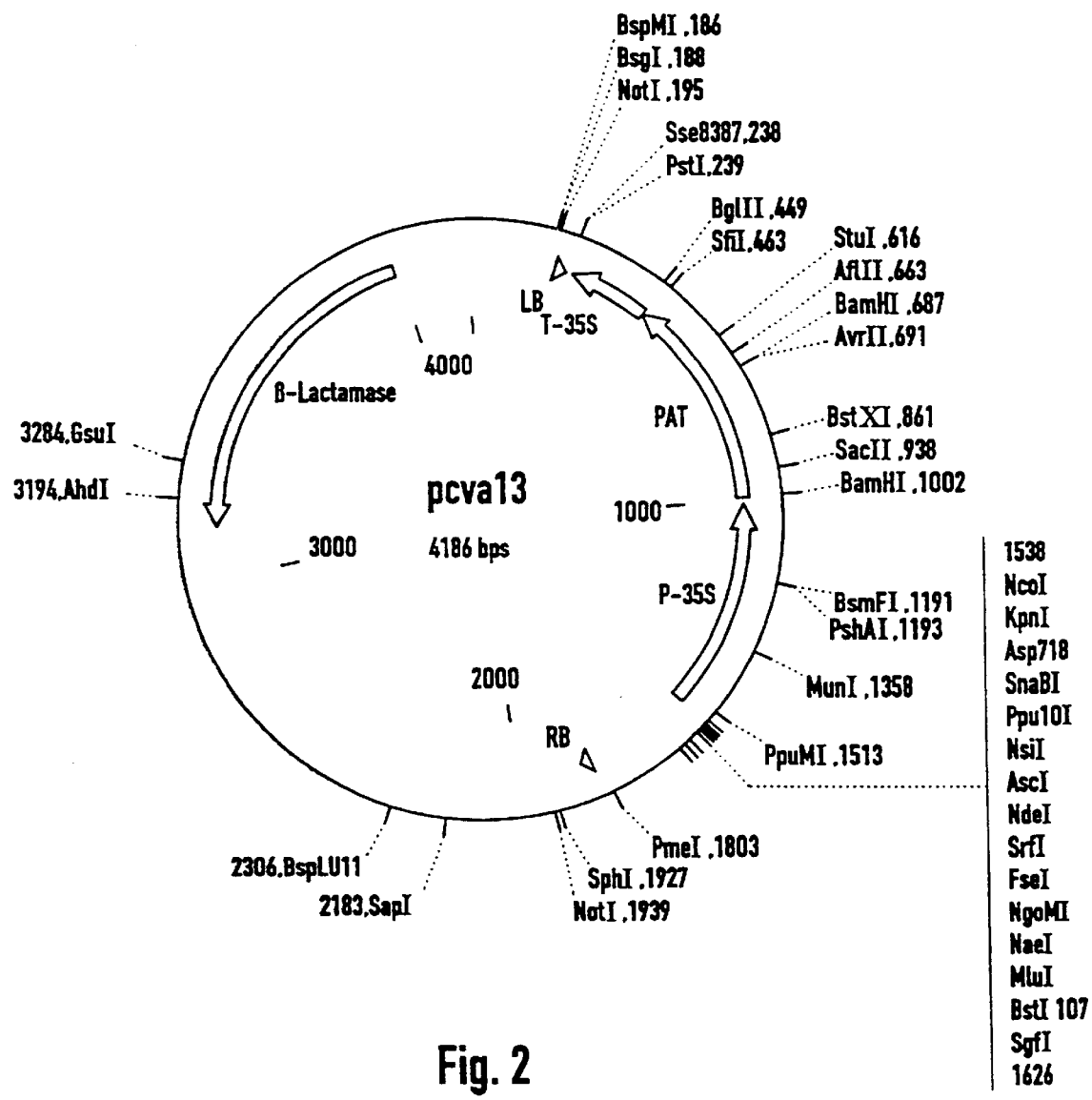
FIG. 2 depicts lasmid pcva13.

The approx. 2.2 kb cassette containing 35S promoter, targeting sequence, ALAS gene and 35S terminator was excised from pALAS2 by means of EcoRI and the overhanging DNA ends of this fragment were filled up by means of T4-DNA polymerase. The vector pcva13 (SEQ ID NO: 8; plasmid map in FIG. 2) was linearized with SnaBI, dephosphorylated by means of alkaline phosphatase and ligated to the approx. 2.2 kb pALAS2 fragment which has been filled up. Amongst the ligation products obtained, one plasmid in which the direction of reading of the hemA gene and the PAT gene are identical, was termed pALAS3f (cf. FIG. 3).

Figure 3:
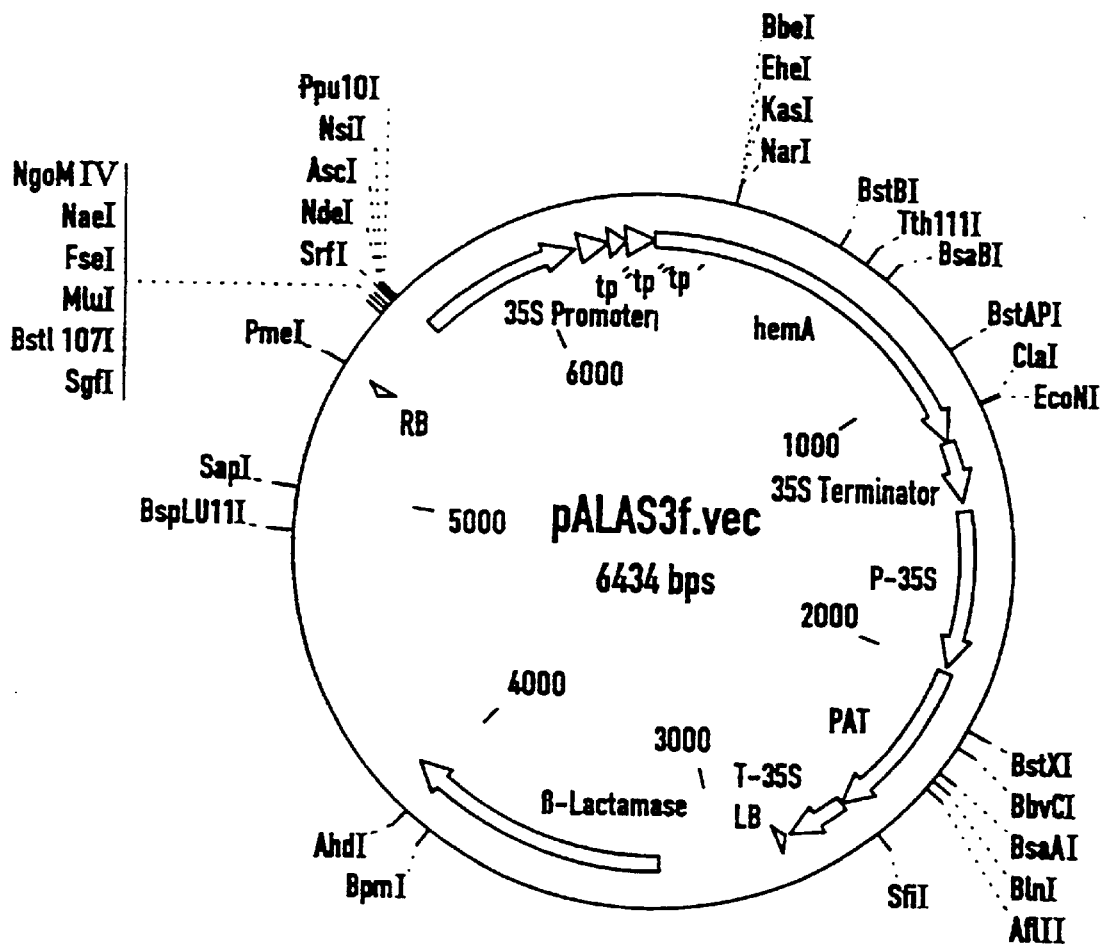
FIG. 3 depicts lasmid pALAS3f.vec.

Key to FIG. 3: The vector pcva13 (amp=beta-lactamase) contains a cassette with the following elements: P-35S= CaMV35S promoter, PAT=phosphinothricin acetyl transferase, T-35S=CaMV35S transcription terminator.

EXAMPLE 2

Production of Plants Which Express the HemA Gene

To produce transgenic maize plants which contain an expression cassette for *Rhodobacter sphaeroides* hemA gene, a transformation was carried out as described in EP-A 0 469 273, with the difference that pALAS3f was employed as the DNA to be transferred. 41 independent maize transformants were obtained. Amongst these lines termed M23T1, M25T1 to M25T13 and M27T1 to M27T27, plants were regenerated as described. The presence of the complete hemA gene was detected in all transgenic plants by means of PCR using the oligodeoxynucleotides ALAS1 and ALAS2 (see Example 1) as PCR primers.

EXAMPLE 3

Phenotypic Characterization of HemA-expressing Plants

First, the tolerance threshold of the untransformed maize line over the GSAAT inhibitor 3-amino-2,3-dihydrobenzoic acid was determined. To this end, the maize seeds were surface-sterilized by washing them under sterile conditions first for 1 minute in 70% ethanol, then for 20 minutes in 5% sodium hypochlorite, 0.1% Tween 20 and subsequently six times briefly in sterile water. The seeds were then placed under sterile conditions on Murashige & Skoog medium (micro- and macronutrients, Sigma GmbH #M5524) containing 90 g/l sucrose and 8 g/l agar and grown for six days at room temperature under daylight fluorescent tubes in a 12-hour-light/12-hour-dark photoperiod until the second leaf emerged. At this stage, the plantlets were transferred to fresh medium with various concentrations of 3-amino-2,3-dihydrobenzoic acid.

After the plants had been grown for a further 10 days, the effect of the inhibitor was recorded. At a 3-amino-2,3-dihydrobenzoic acid concentration of under 5 $\mu$M, the biomass production was unaltered within the normal variations. At 100 $\mu$M 3-amino-2,3-dihydrobenzoic acid, biomass production was markedly reduced and the newly-formed tissue under the effect of 3-amino-2,3-dihydrobenzoic acid showed marked chlorosis. Six days after the medium was changed, the following wet weights were found for the nontransgenic plants (in each case means of 10 individual plants without root and remains of the seed kernel):

0 $\mu$M 3-amino-2,3-dihydrobenzoic acid: 3.89 g
1 $\mu$M 3-amino-2,3-dihydrobenzoic acid 4.15 g
5 $\mu$M 3-amino-2,3-dihydrobenzoic acid 3.82 g
10 $\mu$M 3-amino-2,3-dihydrobenzoic acid 3.12 g
100 $\mu$M 3-amino-2,3-dihydrobenzoic acid 1.53 g The tolerance of transgenic lines to 3-amino-2,3-dihydrobenzoic acid is determined in comparison with the nontransgenic original line. To this end, five regenerate plants per line whose size and root system visually corresponds to the above-described seedlings after six days germination are transferred to media without 3-amino-2,3-dihydrobenzoic acid (one plant) and with 100 $\mu$M 3-amino-2,3-dihydrobenzoic acid (four plants) and grown on. When exposed to 3-amino-2,3-dihydrobenzoic acid, all regenerated plants of the nontransgenic line show marked chlorosis and reduced biomass production in comparison with the untreated control. On the medium without 3-amino-2,3-dihydrobenzoic acid, the transgenic lines show a phenotype which is comparable with the nontransgenic plants under these conditions. However, in the case of most transgenic lines with the ALAS gene according to the invention, none of the regenerated plants in the presence of 100 $\mu$M 3-amino-2,3-dihydrobenzoic acid shows chloroses or reduced growth compared with their respective untreated controls on medium without 3-amino-2,3-dihydrobenzoic acid.

EXAMPLE 4

Recombinant Production and Purification of GSAAT

The mature Hordeum vulgare GSAAT was produced recombinantly in *Escherichia coli* using the sequence ID No. 6. To this end, the *Escherichia coli* strain TG1 (Gibson (1984) PhD Thesis, Cambridge, UK) was transformed simultaneously with the expression plasmid pATE19 (Barry-Lowe et al. (1992) Plant Physiology 99: 1597–1603) and the plasmid pGroESL (Goloubinoff et al. (1989) Nature 337: 4447). Transformed clones were always grown in LB medium (10 g/l tryptone, 5 g/l yeast extract, 5 g/l NaCl) supplemented with 100 mg/l ampicillin and 30 mg/l chloramphenicol.

100 ml of medium were inoculated with a TG1/pATE19/ pGrosESL clone and incubated in a culture flask for 14 hours at 37° C. with shaking. 5 l of medium were inoculated with this culture and grown in culture flasks at 37° C. with shaking to an optical density of $OD_{550}$=0.5. Then, isopropyl-b-D-thiogalactopyranoside was then immediately added to a final concentration of 0.5 mM. At the same time, the incubation temperature was reduced to 28° C. After incubation for a further 16 hours, the cells was harvested by centrifugation (4200 g, 20 min, 4° C.).

The cell sediment was resuspended in 150 ml of buffer A (50 mM tricine/NaOH pH 7.99 25 mM $MgCl_2$). The cells were then disrupted by three passages through the French-Press homogenizer (French Pressure Cell Press and 35 ml disruption cell by SLM Instruments, Inc., Rochester N.Y. 14625 USA) at 16,000 psi and 4° C. The homogenate was then centrifuged for 30 minutes at 25,000 g and 4° C. The clear supernatant was subjected to an anion-exchange chromatography.

For the chromatography, a DEAE-sepharose fast-flow column (Pharmacia GmbH, Freiburg) with a bed volume of 500 ml equilibrated with buffer A. The clear supernatant of the disrupted cells was applied to this column. Then the column was first eluted with 250 ml of buffer A and then with 1500 ml of buffer B (50 mM tricine/NaOH pH 7.9, 25 mM $MgCl_2$, 20 mM NaCl). Elution of the recombinant GSAAT was done with 750 ml of buffer C(50 mM tricine/ NaOH pH 7.9, 25 mM $MgCl_2$, 100 mM NaCl). The eluate was collected in 25-ml-fractions and the fractions which contained functional GSAAT were determined from amongst the fractions by means of subjecting samples to a GSAAT activity test. 5 l of expression culture gave 25 nkat GSAAT.

EXAMPLE 5

Determination of the Enzymatic GSAAT Activity

GSAAT activity was detected by a photometric detection of the derivatized reaction product 5-aminolevulinic acid. The activity test was carried out in a 96-well flat-bottom microtiter plate (F form) made of polystyrene.

It was possible to carry out the desired number of individual measurements in parallel in the wells of the microtiter plate. The following information relates in each case to one well of the microtiter plate (MTP).

At a temperature of 20° C., 100 µl of enzyme solution (25 pkat/ml recombinant Hordeum vulgare GSAAT, 250 mM Bis Tris/HCl pH 6.5) and 10 µl of 25% (v/v) dimethyl sulfoxide in water were introduced into the well. The enzymatic reaction was started by adding 5 µl of 1.8 mM glutamate-1-semialdehyde dissolved in 100 mM HCl.

Immediately after the enzymatic reaction had started, the mixture was incubated for 30 minutes at 20° C. Then, 25 µl of ethyl acetoacetate were added immediately, and the mixture was mixed thoroughly and incubated for 30 minutes at 40° C. Immediately thereafter, 100 µl of Ehrlich's reagent (see below) were added and the mixture was incubated for 30 minutes at 20° C. After the incubation had ended, the absorption of the solution was determined immediately at a wavelength of 540 nm with the aid of a microtiter plate photometer.

To determine the enzymatically formed quantity of 5-aminolevulinic acid, the blank value (see below) was first deducted from the absorption of the mixture to be analyzed. The difference between measured value and blank value was used for calculating, with the aid of a calibration series, the concentration of 5-aminolevulinic acid in the reaction mixture at the time immediately prior to addition of the ethyl acetoacetate. The calibration series was generated by first incubating in each case 100 µl of 5-aminolevulinate solutions of different concentrations in 250 mM Bis Tris/HCl pH 6.5 for 30 minutes at 20° C., then mixing them with 25 µl of ethyl acetoacetate, incubating them for 30 minutes at 40° C., subsequently treating them with 100 µl of Ehrlich's reagent, then incubating them for 30 minutes at 20° C., and determining the absorption of the resulting solution immediately with the aid of a microtiter plate photometer at a wavelength of 540 nm. The 5-aminolevulinic acid concentration in 100 µl of 250 mM Bis Tris/HCl pH 6.5 is varied during this procedure in parallel mixtures between 0 µM and 150 µM (0 µM, 5 µM, 10 µM, 20 µM, 50 µM, 100 µM, 150 µM). To determine a blank value (see above) as reference for the measured absorption value of a GSAAT reaction, a parallel GSAAT activity test was carried out in which 1.) the enzymatic GSAAT activity was blocked and which 2.) was otherwise carried out under exactly the same conditions as the comparison mixture. To block the GSAAT activity, 10 µl of a solution of 10 mM aminooxyacetic acid in 25% (v/v) dimethyl sulfoxide/water instead of 10 µl of 25% (v/v) dimethyl sulfoxide/water (see above) are introduced before the start of the reaction, together with the enzyme solution.
Composition of Ehrlich's Reagent:
Dissolve 1 g of 4-dimethylaminobenzaldehyde in 30 ml of glacial acetic acid and subsequently mix with 8 ml of 70% perchloric acid. Bring to a final volume of 50 ml with glacial acetic acid.

EXAMPLE 6

Identification of GSAAT Effectors

To find novel GSAAT effectors, a number of different chemical substances was screened for their action. This does not include substances or compounds which exhibited unfavorable chemically-reactive properties under the conditions of the GSAAT activity test, for example which cause alkylation, halogenation, oxidation, reduction or other unspecific covalent modifications of proteins or of the enzyme substrates applied. The compounds were dissolved in 25% (v/v) DMSO/water in a concentration of 100 µM.

To determine the action of these compounds on the enzymatic GSAAT activity, 10 µl of the 100 µM solution of each compound was put into a well of a 96-Well MTP (see above). 90 wells of an MTP were thus provided with solutions of the test compounds. To determine the activity of noninhibited GSAAT (control reaction), 10 µl of 25% (v/v) DMSO/water were introduced into 3 wells of the same MTP, and, to determine blank values, in each case 10 µl of a solution of 10 mM aminooxyacetic acid in 25% (v/v) dimethyl sulfoxide/water were introduced into the remaining 3 wells.

The solutions in the MTP wells were then mixed with in each case 100 µl of enzyme solution (25 pkat/ml recombinant Hordeum vulgare GSAAT, 250 mM Bis Tris/HCl pH 6.5). The enzymatic reaction was started in all wells of an MTP at the same time by adding 5 µl of 1.8 mM glutamate-1-semialdehyde dissolved in 100 mM of HCl. The next steps were identical to the procedure described under Example 2 after the start of the enzymatic reaction.

It was then possible to determine the activity of the noninhibited GSAAT for each MTP from the mean of the readings for the wells with the control reactions and the mean of the wells with the blank values. Also, the GSAAT activity was determined for each well of this MTP in which a test substance was employed by subtracting the mean of the blank values. A comparison of GSAAT activity in the presence of a test substance and the activity in the absence of the test substance (control reactions) determined whether the substance has an effector, i.e. inhibitory or activating efficacy on the GSAAT activity test.

Compounds which cause a relative reduction in GSAAT activity by more than 30% compared with the control reactions were considered as potential effectors and as such examined in greater detail.

EXAMPLE 7

Determination of the Efficacy Level of the GSAAT Effectors

The efficacy level of a GSAAT effector was determined by carrying out the GSAAT test (cf. Example 2) in the presence of various effector concentrations in the reaction solution. Concentrations of 1 nM, 3 nM, 10 nM, 30 nM, 100 nM, 300 nM, 1 µM, 3 µM, 10 µM, 30 µM, 100 µM and 300 µM of the effector were employed. The inhibitor constants were calculated by the methods described extensively by Bergmeyer using the activities deduced from the readings (Grundlagen der enzymatischen Analyse [Basics of Enzymatic Analysis]; Ed. Hans Ulrich Bergmeyer, Verlag Chemie Weinheim, New York, 1977, ISBN 3-527-25677-6), and the constants for activators were determined analogously.

EXAMPLE 8

Lemna Test

The phytotoxic action of GSAAT inhibitors was also determined in vivo by treating Lemna cultures.

To this end, *Lemna gibba* was cultured in sterile culture solution (0.4 g/l $KNO_3$, 0.8 g/l $CaCl_2*2H_2O$, 0.366 g/l $MgSO_4*7H_2O$, 0.2 g/l $KH_2PO_4$, 2 ml/l solution I (2.23 g/l $MnSO_44H_2O$, 83 mg/l Kl, 2.5 mg/l $CoCl_2*6H_2O$, 0.86 g/l $ZnSO_4*7H_2O$, 2.5 mg/l $CuSO_4*5H_2O$, 0.62 g/l $H_3BO_3$, 25 mg/l $Na_2MoO_4*2H_2O$) and 2 ml/l solution II(14.92 g/l Na-EDTA, 10.92 g/l $FeSO_4*7H_2O$)). In each case 3 plants were placed under sterile conditions into the a 100 ml Erlenmeyer flask which was filled with 50 ml culture solution containing the GSAAT inhibitor in a concentration of 20 $\mu$M. The culture flasks were illuminated at 25° C. with two 36 W daylight fluorescence tubes at a distance of 70 cm (24-hour light photoperiod). Growth and phenotype of the Lemna plants were observed over 7 days and compared with the growth and the phenotype of Lemna plants which had been grown in culture solution without inhibitor under otherwise identical conditions. It was characteristic of the phytotoxic effect of a GSAAT inhibitor that the newly-formed tissues were chlorotic. When light intensities were high, it was also possible for the plant tissue to become necrotic. Compounds with a rapid action frequently led to complete destruction of the plants after only one day, while the more slowly acting compounds first led to growth depression.

EXAMPLE 9

GSAAT Inhibitors

The above-described method allowed the following herbicidally active compound A (hydrazinopropylsulfonic acid, sulfopropylhydrazine) to be found:

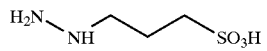

At a concentration of 6 $\mu$M, compound A leads to a 50% reduction in GSAAT activity.

In the Lemna test, compound A led to chloroses and growth depression of the plants within 48 hours. After 72 hours, over 60% of the plants had died.

What is claimed is:

1. A method for producing a transgenic monocotyledonous plant, its cells, its parts, its seeds, and its propagation material, comprising the step of introducing into a monocotyledonous plant one or more nucleic acid molecules encoding a 5-aminolevulinic acid synthase (ALAS) isolated from the alpha group of purple bacteria, whereby the one or more nucleic acid molecules are stably integrated into the plant genome.

2. The method as claimed in claim 1, wherein the one or more nucleic acid molecules encoding an ALAS are stably integrated into the plant plastome by plastid transformation.

3. A method for expressing an ALAS in transgenic monocotyledonous plant cells or plants, comprising the step of introducing into the plant cells or plants at least one nucleic acid molecule encoding an ALAS isolated from the alpha group of purple bacteria. whereby the nucleic acid molecule is expressed in the plant cells or plants.

4. A method for producing transgenic plant cells or plants whose glutamate-1-semialdehyde transferase (GSAAT) expression is suppressed or inhibited, and wherein the plant is a monocotyledonous plant, comprising the step of introducing at least one nucleic acid molecule encoding an ALAS isolated from the alpha group of purple bacteria into the plant plastome by plastid transformation, whereby the nucleic acid molecule is stably integrated into the plant plastome.

5. A non-naturally occurring chimeric gene, containing at least a promoter for driving expression in plants, functionally linked to a DNA molecule encoding an ALAS isolated from the alpha group of purple bacteria.

6. The non-naturally occurring chimeric gene according to claim 5, wherein the nucleic acid molecule encoding the ALAS is isolated from *Rhodobacter sphaeroides*.

7. A transgenic monocotyledonous plant, its cells, its parts, its seed or its propagation material, each containing a DNA molecule encoding a protein with the function of an ALAS isolated from the alpha group of purple bacteria.

8. The method as claimed in claim 1 wherein said nucleic acid molecules are under the control of a feedback-regulated promoter.

9. The method as claimed in claim 2 wherein said nucleic acid molecules are under the control of a feedback-regulated promoter.

10. The method as claimed in claim 8 wherein the feedback-regulated promoter controls the presence of the ALAS in the transgedic plant, its cells, its parts, its seeds, and its propagation material, and wherein (a) ALAS synthesis rate is sufficiently high for physiologically necessary porphyrin biosynthesis, and (b) ALAS production is not damaging to the plant directly or indirectly.

11. The method as claimed in claim 9 wherein the feedback-regulated promoter controls the presence of the ALAS in the transgenic plant, its cells, its parts, its seeds, and its propagation material, and wherein (a) ALAS synthesis rate is sufficiently high for physiologically necessary porphyrin biosynthesis, and (b) ALAS production is not damaging to the plant directly or indirectly.

12. A recombinant vector containing the chimeric gene as claimed in claim 6.

13. A recombinant vector containing the chimeric gene as claimed in claim 6.

14. A transgenic monocotyledonous plant cell which is transformed and/or genetically modified with the chimeric gene as claimed in claim 5.

15. A transgenic monocotyledonous plant cell which is transformed and/or genetically modified with the chimeric gene as claimed in claim 6.

16. A plant, plant cell, plant part, plant seed or propagation material produced by the method as claimed in claim 1.

17. A plant, plant cell, plant part, plant seed or propagation material produced by the method as claimed in claim 2.

18. The plant cell as claimed in claim 14 wherein the plant cell is a maize plant cell.

19. The plant as claimed in claim 16, wherein the plant is a maize plant.

20. A method for controlling undesired vegetation in planting areas of monocotyledonous plants comprising the steps of producing a transgenic monocotyledonous plant according to the method of claim 1, and applying an herbicidal composition, whose mechanism of action is based at least in part on inhibition of plant GSAAT, to the transgenic plant or its propagation material.

\* \* \* \* \*

SEQUENCE LISTING

<160> NUMBER OF SEQ ID NOS: 10

<210> SEQ ID NO 1
<211> LENGTH: 3681
<212> TYPE: DNA
<213> ORGANISM: Rhodobacter sphaeroides
<220> FEATURE:
<221> NAME/KEY: gene
<222> LOCATION: (1947)..(3170)
<223> OTHER INFORMATION: nucleotide sequence of hemA
<308> DATABASE ACCESSION NUMBER: L07490
<309> DATABASE ENTRY DATE: 1994-02-28
<313> RELEVANT RESIDUES: (1)..(3681)

<400> SEQUENCE: 1

```
ggatcctgct cgcccacgag gcggaagctg accttggcat gggcctcggc gggcagcacc        60
gtcttgaagc ccgccccggt atagccgccc cagatgccgt tgatctcgca ggtggggcgc       120
gaccagatca tctcgagggg tgtgcgatcc tcttcgcctg cgggctgcga gaggcccacg       180
tcgccgagga agcgcgcgtg atcgaaggcg agccctgcc actgggcgcg gatcgcctcg       240
ggcaattcgc tcacgccgtc gtagaagccg ggcagggtga cgcggccggt ctcgtcgtga       300
agggccgcga gcgcgcgggt cagcacgcgg atcgggttga tcgcgacccc gccatacatg       360
ccggaatgca ggtccttcga ggggccgcgc accaccagct cctcgcccag caggccgcgc       420
agcatggtca cgatggcggg cgtgcgcgat tcgaagaggc cggtgtcgca gatcagcgcc       480
acatccgcgg tcagctcttc ggcattctcc ttcatgaagg gcacgagcga gggcgagccc       540
gattcctcct cgccctcgag gaagatcgtg aggcggcagg gcagcgtgcc gtgctcggcc       600
ttccaggcgc ggcaggcctc gaggaaggtc atgagctggc ccttgtcgtc ggaggcgccg       660
cggccgcgga tcaccttgcc gcgcggcgtc tcctcgatcg ccggctcgaa gggcggacgg       720
tcccagagcg agagcggatc gacgggctgc acgtcgtaat ggccgtagaa cagcaggtgc       780
ggcccttgac ccggggcatg agccaccacc atcggatggc cggggggtggg gcgcttcgag       840 acctcgaagc ccagcgacgc gagatcggcc accagccagt cggcggcggc ctcgcattcg       900
gcggcatggg cgggatcggt cgagatcgag gggatgcgca acagcgccat cagccggtcc       960
agagcctcgg gcaggccggt gtcgatccgg gtgagcacgg cgtcgagcgt catcgtctgg      1020
```

-continued

```
tccttccacg tccaatgtgt ccgccgcagc acggcgggcg gagcggtgcc cttcgccgga    1080
ctcggctcct gcgcgtcccg gtatgggccg cggctaaggg cgaagtcaat ttggaggatg    1140
gccgtggggc agggcggggg gcgttcacaa gacggggagg ctctgtgcag gaggggcgcg    1200
gtgggctaag agggccgcga cagggtgcag gtggagagga tcatgcgtct ggcaatggtg    1260
gcagccctcg ggatcttgac ggcgggggct gcgctcgccc agccggtgac gggccgcgag    1320
gcgaagaaga tgctctttcc ccccgcgaag gccgaggtgg agatcctgcc ggtcgccttc    1380
ctctccgaga acgaccgcgc gctcctgcgc atggtggtga gcgagcagcc ctattacggg    1440
gccatcgccg tctcgcccga tgaggggctg gcctcggagg cgaccatcgc ggccgcgaac    1500
catcacacga ccgaggccgc ggcgcgcgcc gcgctcgcgg tctgcgagga gaagcgcaag    1560
ggcagggcgc cgtgcgcgat cgtgggattc gtgcgcccca agggctggaa gagccgcccg    1620
ctcagcctat cgtccgatgc aaccgaggga ttccggggccg actatggcgc ccgcggcccg    1680
agggcgctgg cggtctcgcc ggccaccggg cgctggggca tcgggaccgg agcggggggcg    1740 ggagagaagg cgcttgctgc ctgcgcgaag gccgaggggcg ccggggattg cgtgctggcg    1800
gtggccgatt gacgcaggga ccaatgaacg ggtttcaaat tggccggttc cagacttagg    1860
atttgatcct tatcaaggcc atgttgcgcc gaaaattgat gatgacaccc agcttgctcg    1920
gcagcccgag cgtcagggag acgaagatgg actacaatct ggcactcgat accgctctga    1980
accggctcca taccgagggc cggtaccgga ccttcatcga catcgagcgg cgcaagggtg    2040
ccttcccgaa agccatgtgg cgcaagcccg acgggagcga gaaggaaatc accgtctggt    2100
gcggcaacga ctatctcggc atgggccagc atccggtggt gctgggggcc atgcacgagg    2160
cgctggattc gaccggcgcc gggtcgggcg gcacgcgcaa catctcgggc accacgctct    2220
atcacaagcg cctcgaggcc gagctcgccc acctgcacgg caaggaagcg gcgctggtct    2280
tctcgtcggc ctatatcgcc aacgacgcga ccctctcgac gctgccgcag ctgatcccgg    2340
gcctcgtcat cgtctcggac aagttgaacc acgcttcgat gatcgagggc atccgccgct    2400
cgggcaccga gaagcacatc ttcaagcaca atgacctcga cgacctgcgc cggatcctga    2460
cctcgatcgg caaggaccgt ccgatcctcg tggccttcga atccgtctat tcgatggatg    2520
gcgacttcgg ccgcatcgag gagatctgcg acatcgccga cgagttcggc gcgctgaaat    2580
acatcgacga ggtccatgcc gtcggcatgt acggccccccg cggcggcggc gtggccgagc    2640
gggacgggct gatggaccgg atcgacatca tcaacggggac gctgggcaag gcctatggcg    2700
tgttcggcgg ctatatcgcg gcctcgtcaa agatgtgcga cgcggtgcgc tcctacgcgc    2760
cgggcttcat cttctcgacc tcgctgccgc ccgtcgtggc ggccggtgcg gcggcctcgg    2820
tgcgccacct caagggcgat gtggagctgc gcgagaagca ccagacccag gcccgcatcc    2880
tgaagatgcg cctcaagggg ctcggcctgc cgatcatcga ccacgctcg cacatcgtgc    2940 cggtccatgt gggcgacccc gtgcactgca agatgatctc ggacatgctg ctcgagcatt    3000
tcggcatcta tgtccagccg atcaacttcc cgaccgtgcc gcgcgggacc gagcggctgc    3060
gcttcacccc gtcgcccgtg catgattccg gcatgatcga tcacctcgtg aaggccatgg    3120
acgtgctctg gcagcactgt gcgctgaatc gcgccgaggt cgttgcctga cagcttctgc    3180
ggatgcaaag gcccctgccc tgtgctactt cttcgggac agggcacccc tgagtcggaa    3240
gcaaccggcc ggggtaaatc ggggcaggac gggcacacgg atgatctggc ggaggacaca    3300
accttcgacg gccgaagtcg ataaacccaa agggttcgac gatttcgagt tgcggttggg    3360
```

-continued

| | |
|---|---|
| cgacctgatg cgcggtgagc gggcgacgct cggcaagtcg ctgctcgatg tccagcgcga | 3420 |
| gctgaagatc aaggccacct atatcgccgc catcgagaat gccgacgtgt cggccttcga | 3480 |
| gacgcagggc ttcgtggcgg gatatgtgcg ctcctatgcg cgctatctcg gcatggaccc | 3540 |
| ggacgaggcc ttcgcgcgct tctgccacga ggcgaacttc accacgatgc acggcatggc | 3600 |
| cgtttcggtg accggcgcgc gccgcgatac cggtccgcgg tcccgaccgc agggcgaggg | 3660 |
| gcgcgatccg ctggcggatc c | 3681 |

<210> SEQ ID NO 2
<211> LENGTH: 1881
<212> TYPE: DNA
<213> ORGANISM: Rhodobacter sphaeroides
<220> FEATURE:
<221> NAME/KEY: gene
<222> LOCATION: (407)..(1630)
<223> OTHER INFORMATION: nucleotide sequence of hemT
<300> PUBLICATION INFORMATION:
<308> DATABASE ACCESSION NUMBER: L07489
<309> DATABASE ENTRY DATE: 1994-03-26
<313> RELEVANT RESIDUES: (1)..(1881)

<400> SEQUENCE: 2

| | |
|---|---|
| catggttcgc ttctcggtgc ggccggatcg ttcggaacgc cggcggagga tcgggtgcca | 60 |
| cgccagaaga gacggcgcat cgggaacgga gaccggacgc aagggaagac tggcccatcg | 120 |
| agcgcgtcag gttgaacaga gactcacggc acgcgccgta cctacaccca tacaaatctc | 180 |
| tgttcaatgt atggttcatg tcttcgtggg gaagaagggg ggcccccctat tctctaacaa | 240 |
| tgtccaggga agtgtcggca cgtttcgccg cgcatcacgc gtgcgtcagg agtgtcagcg | 300 |
| gcaaaatgtc cgttgattca tccagattgt aagccataca aatggccgat aggcggctcg | 360 |
| gcaatgcctg ccgcgatgcg tgtcgctcca acagaaggtg atccccatgg agttctctca | 420 |
| gcacttccag aagctcattg acgacatgcg actggacggg cggtacagga cgttcgcgga | 480 |
| actcgagcgc atcgccgggg agtttccgac cgcgctctgg catggtccgg acgggcaggc | 540 |
| cagacgcgtg acggtctggt gcagcaacga ctatctgggc atgggccaga acgccgaagt | 600 |
| gctggccgcg atgcaccggt cgatcgatct gtcgggcgcc ggcaccggag gcacccgcaa | 660 |
| catctcgggg accaaccggc agcacgtcgc cctcgaggcg gaacttgcgg acctgcacgg | 720 |
| caaggaatcc gcgctcatct tcacctccgg gtggatctcc aacctcgcgg ctctgggcac | 780 |
| gctgggcaag attctgcccg aatgcgcgat cttctcggat gcgctgaacc acaattcgat | 840 |
| gatcgagggc atccgccggt ccggcgccga gcgcttcatc ttccaccaca cgatcccgt | 900 |
| ccatctggac cggttgcttt cgtccgtcga tccggcgcgc ccgaagatcg tggccttcga | 960 |
| aagcgtctac agcatggacg cgacatcgc cccatcgcc gaaatctgcg acgtggccga | 1020 |
| gcggcatggt gcgctgacct atctcgacga ggttcatgcg gtcggacttt acggcccgcg | 1080 |
| cggcggcggc atcagcgacc gcgacgggtt ggcggatcgg gtgacgatca tcgagggcac | 1140 |
| gctcgccaag gctttcggcg tgatgggcgg ctatgtcagc ggcccgtccc tgctgatgga | 1200 |
| tgtgatccgc agcatgtccg acagtttcat cttcaccacc tcgatctgcc cgcacctcgc | 1260 |
| ggcggggcc ctcgcggcgg tccggcatgt gaaggctcat cccgacgagc cgccggca | 1320 |
| ggcggagaat gcggtgcgcc tcaaggtcct gctgcagaag gccggtctcc cggttctcga | 1380 |
| cacgcccagt cacatccttc ccgtgatggt gggcgaggcg catctctgcc gcagcatcag | 1440 |
| cgaggcgttg ctcgcccgcc acgccatcta cgtccagccg atcaactatc cgaccgtggc | 1500 |
| tcgggggcag gagcggtttc ggctgacgcc gacgcccttc catacgacgt ctcacatgga | 1560 |

-continued

```
ggcactggtc gaggcgctcc tcgccgttgg ccgggatctc ggatgggcca tgtcgaggcg   1620
ggctgcctag gcaggagcca ccaccggctc tcggtcccgt ggccggcgcc tgcgcgggat   1680
cgaagcgctc tcgcccgccg gccatgcgca acggacccgg gtgccggaag acacgccatc   1740
ggatccggca aggacggcgt gttcgtcgcg gagggcaccc ggacaggcgc tgcgggatcc   1800
ggcgccgtca tcctctcggc cggagagatc gccttgatcc ggcatccccc gaagccgtgg   1860
acgcgccgtg cctgcctgca g                                             1881
```

```

<210> SEQ ID NO 3
<211> LENGTH: 1320
<212> TYPE: DNA
<213> ORGANISM: Rhodobacter capsulatus
<220> FEATURE:
<221> NAME/KEY: gene
<222> LOCATION: (71)..(1276)
<223> OTHER INFORMATION: nucleotide sequence of hemA
<300> PUBLICATION INFORMATION:
<308> DATABASE ACCESSION NUMBER: X53864
<309> DATABASE ENTRY DATE: 1996-10-07
<313> RELEVANT RESIDUES: (1)..(1320)

<400> SEQUENCE: 3
tgcgcgccgg acagggccga agagccgacc cggcaaacca caaccagcag caaagccagg     60
ggtgacgcac atggactaca atctcgcgct cgacaaagcg atccagaaac tccacgacga    120
gggacgttac cgcacgttca tcgacatcga acgcgagaag ggcgccttcc ccaaggcgca    180
gtggaaccgc cccgatggcg gcaagcagga catcaccgtc tggtgcggca acgactatct    240
gggcatgggc cagcacccgg tcgttctggc cgcgatgcat gaggcgctgg aagcggtcgg    300
ggccggttcg ggcggcaccc gcaacatctc gggcaccacg gcctatcacc gccgtctgga    360
agccgagatc gccgatctgc acggcaagga agcggcgctt gtcttctcct cggcctatat    420
cgccaatgac gcgacgctct cgacgctgcg gctgcttttc cccggcctga tcatctattc    480
cgacagcctg aaccacgcct cgatgatcga ggggatcaag cgcaatgccg ggccgaagcg    540
gatcttccgt cacaatgacg tcgcccatct gcgcgagctg atcgccgctg atgatccggc    600
cgcgccgaag ctgatcgcct tcgaatcggt ctattcgatg gatggcgact tcggcccgat    660
caaggaaatc tgcgacatcg ccgatgaatt cggcgcgctg acctatatcg acgaagtcca    720
tgccgtcggc atgtatggcc cccgcggcgc gggcgtggcc gagcgtgacg gtctgatgca    780
ccgcatcgac atcttcaacg gcacgctggc gaaagcctat ggcgtcttcg gcggctacat    840
cgccgcttcg gcgaagatgg tcgatgccgt gcgctcctat gcgccgggct tcatcttctc    900
gacctcgctg ccgccggcga tcgccgctgg cgcgcaggcc tcgatcgcgt ttttgaaaac    960
cgccgaaggg cagaagctgc gcgacgcgca acagatgcac gcgaaggtgc tgaaaatgcg   1020
gctcaaggcg ctggggatgc cgatcatcga ccatggcagc cacatcgttc cggtggtcat   1080
cggtgacccc gtgcacacca aggcggtgtc ggacatgctc ctgtcggatt acggcgttta   1140
cgtgcagccg atcaacttcc cgacggtgcc gcgcggcacc gaacggctgc gcttcacccc   1200
ctcgccggtg catgacctga aacagatcga cgggctggtt catgccatgg atctgctctg   1260
ggcgcgctgt gcgtgaatcg cgccgaggcc tctgcctgag ccattctgcg gatgcaccgc   1320
```

```

<210> SEQ ID NO 4
<211> LENGTH: 2117
<212> TYPE: DNA
<213> ORGANISM: Saccharomyces cerevisiae
<220> FEATURE:
```

<220> NAME/KEY: gene
<222> LOCATION: (221)..(1867)
<223> OTHER INFORMATION: nucleotide sequence of HEM1
<300> PUBLICATION INFORMATION:
<308> DATABASE ACCESSION NUMBER: M26329
<309> DATABASE ENTRY DATE: 1993-04-23
<313> RELEVANT RESIDUES: (1)..(2117)

<400> SEQUENCE: 4

| | | | | | |
|---|---|---|---|---|---|
| atactctatt | cggttgtgtg | ttgcaccctg | ctctgctgtc | tctcaaccgt | tcttccttta | 60 |
| cacgccttcc | cttctcagct | cgcgtttctt | tttttttat | cccactcttt | tcttttttct | 120 |
| ttcctatata | ttgcccatat | aagtttggtt | ggaaggaaaa | ctaatagagc | tagttgttgt | 180 |
| ccctcaataa | tcataacagt | acttaggttt | tttttcagt | atgcaacgct | ccattttgc | 240 |
| gaggttcggt | aactcctctg | ccgctgtttc | cacactgaat | aggctgtcca | cgacagccgc | 300 |
| accacatgcg | aaaatggct | atgccaccgc | tactggtgct | ggtgccgctg | ctgccactgc | 360 |
| cacagcgtca | tcaacacatg | cagcagcagc | agcagccgct | gctgccaacc | attccaccca | 420 |
| ggagtcgggt | ttcgattacg | aaggcctgat | agattccgaa | ctgcagaaga | aaagacttga | 480 |
| caaatcgtac | agatatttca | acaatatcaa | ccgattggcc | aaggagttcc | ccctagctca | 540 |
| tcgccagaga | gaggcggaca | aggtcaccgt | ttggtgttcc | aacgactatt | tagcactttc | 600 |
| caagcaccct | gaggtattgg | acgccatgca | taaaactatc | gacaagtatg | ttgtggtgc | 660 |
| cggtggtaca | agaaacattg | ctggccataa | catccccact | ttgaatctgg | aagccgaatt | 720 |
| ggccactta | cacaagaagg | aaggtgcctt | agttttttcg | tcatgttacg | tagccaacga | 780 |
| tgccgtctta | tccctactgg | gtcaaaagat | gaaggacttg | tgattttct | ccgacgaact | 840 |
| caaccatgcg | tccatgattg | tcggtattaa | gcatgctaac | gtaaaaaaac | acattttcaa | 900 |
| acataatgac | ttgaacgaat | tggaacaact | gctccagtca | taccccaaat | ccgttcctaa | 960 |
| actaattgct | ttcgaatcag | tatattctat | ggccggttca | gtggccgaca | tagaaaaaat | 1020 |
| ttgcgacttg | gccgacaaat | acggtgcttt | gaccttcttg | gatgaagtac | atgcggtcgg | 1080 |
| cctgtacgg | cctcacggtg | caggtgttgc | agaacattgt | gattttgaaa | gtcaccgtgc | 1140 |
| aagtggtatt | gctaccccaa | agaccaatga | caagggcggc | gcgaagactg | tgatggaccg | 1200 |
| tgtcgacatg | atcaccggca | ctttaggtaa | gtctttcggt | agcgtaggtg | gctacgtcgc | 1260 |
| agcctctagg | aaattgatcg | attggttcag | atcgtttgca | cctggtttca | ttttcaccac | 1320 |
| gactttacca | ccttcagtta | tggcaggcgc | taccgcagca | attagatacc | aacgttgcca | 1380 |
| catcgaccta | agaacctcgc | aacagaaaca | taccatgtac | gtaaagaaag | ctttccatga | 1440 |
| gttgggcatt | ccagttattc | caaatccttc | tcatatcgtc | ccagtgttga | ttggtaatgc | 1500 |
| tgatttggct | aagcaagctt | ctgacatctt | aatcaataag | catcaaatct | acgtacaagc | 1560 |
| tatcaacttc | cctacggttg | ctcgcggtac | cgaaagattg | agaattaccc | caacgccagg | 1620 |
| tcacaccaac | gatttatctg | acatcttaat | caatgcagtt | gatgatgtgt | tcaatgagct | 1680 |
| acagttacca | cgtgtcagag | actgggaaag | ccaaggtggc | ttattgggtg | ttggagagag | 1740 |
| cggatttgtg | gaagagtcta | acttatggac | atcaagccaa | ctatctttaa | ctaatgacga | 1800 |
| cttgaaccct | aatgttagag | accccatcgt | taaacaacta | gaggtttcta | gtggtatcaa | 1860 |
| gcagtaaaac | aaccaatata | tgcatgggct | gagatagagg | tacaaggaat | ttgtaaatca | 1920 |
| gtaaaaaaaa | aaattaacag | ttttttttt | tcatttttt | ttttattctt | atttatgtat | 1980 |
| gatactttat | tattatttct | cttaattatt | tatttattta | actaacacga | tgagcacttt | 2040 |
| taactgcaat | ggttaaactg | tagcaatgtt | ggtaaaaaag | cagggaaagt | tcaaaaataa | 2100 |

```
tttatgtatt tttcctc                                           2117
```

<210> SEQ ID NO 5
<211> LENGTH: 2416
<212> TYPE: DNA
<213> ORGANISM: Arabidopsis thaliana
<220> FEATURE:
<221> NAME/KEY: gene
<222> LOCATION: (405)..(2259)
<223> OTHER INFORMATION: nucleotide sequence of GSA2
<300> PUBLICATION INFORMATION:
<308> DATABASE ACCESSION NUMBER: U10278
<309> DATABASE ENTRY DATE: 1995-10-11
<313> RELEVANT RESIDUES: (1)..(2416)

<400> SEQUENCE: 5

```
tgaaaaagaa catacatttt cataatcaaa ttatgatata ttctaccaaa ttataagcaa     60
aggaaaatta taatctagtc attatttata catgttatat ttgaattcac gtttgtatcc    120
attacaaaaa tttatgtaat tcgcagaaaa tatatatatg tcaaattaag ttatcggacc    180
ggatcgggtc aaagaaaccg gattggttaa caaagtcaaa caaacaaata ttgacttgag    240
tttcagattc cagtaaaatc aaaccggatc gggtctgaat ttaaaccacc gggtcggctc    300
catctaaaat ctgaagatca tctccgcctt atcttgttga ctatctctgt actacttacg    360
agcgcaagtg agagagtaac agagaaacgt agagatatag caaaatggct gcgacgctta    420
ctggatcagg gattgctcta ggttttcgt cgtccgcaaa gttctctaag agagcttctt     480
cgtcgtccaa ccgtcgctgc atcaagatgt cggtttcggt agaggagaag acgaagaaat    540
tcactcttca gaaatctgag gaagctttca tgctgcgaa ggttaggctt ttcaatttcc     600
atgaattcag tcaataagaa atgtttcttc agattgatta cgccttgatg ttctgttgct    660
ttggttttgt gggatttgat catattttg gttaaagtga ttatctttgt tacccttcaa     720
ggaacattgc taacaaaata agattacttg agatagaatc ataatctgag ataaagtttt    780
tgtttttatt cggtttcatt ctgttctgat tattgaaatt ggtttggttc ctttgtgtag    840
aacttaatgc ctggaggtgt gaactcacct gtacgtgctt tcaaatctgt tggtggacaa    900
ccagtggtga tggattctgc aaagggctca cgaataagag acattgatgg aaatgaatac    960
attgactatg ttggatcttg gggacctgct ataattggtc atgctgatga tgaggtttgt   1020
ttctttccag ttttgatgat ttttagatag ctgaaagttt agtagttgat acggtgatgt   1080
gtctagtgca ggttcttgct gctttggctg agacaatgaa gaaaggaaca agctttggtg   1140
ctccttgtct cttagagaat gttcttgctg agatggtgat ttcagctgtt ccaagtattg   1200
aaatggttcg gtttgttaac tccggtacag aggcatgtat gggtgtgcta cgtcttgctc   1260
gtgccttcac agggaaacaa aagttcatca gtttgaagg ttgttatcat ggtcatgcaa     1320
aatctttcct tgtcaaagca ggtagtggtg tagctacttt gggtctacct gactcgcctg   1380
gggtccccaa agcagctact tcagatactt taacagctcc atacaatgat attgctgctg   1440
ttgagaagct ttttgaggca aacaaaggag agattgctgc catcattctt gaacctgttg   1500
ttggtaactc gggttttatt acacctaaac cagagttcat tgagggaata cgccggatca   1560
ctaaagacaa tggtgctctt cttatttttg atgaagtcat gactggtttt cgtttagcct   1620
atggtggagc tcaagagtac tttggaatca cacctgactt aacaactctt gggaaaatca   1680
tcggtggtgg tctcctgtgt ggagcatacg gtggaagaag agacatcatg gaaatggtaa   1740
agctagagtt gttaacaatt gaaccgaata atcttttgaa tttgctgcaa gagattggaga  1800
```

-continued

| | |
|---|---|
| aagtcctgat cctttatcac tcatgtctttt ttgcaggttg cacccgcagg accgatgtat | 1860 |
| caagctggta cgctaagtgg taatccgttg gctatgacag cgggtataca cacgctgaag | 1920 |
| cggttaagtc agccagggac atatgaatac ttagacaaga tcacaaaaga gcttacaaat | 1980 |
| gggatactag aagccgggaa gaaaaccggg catgcgatgt gtggcggtta cataagcggg | 2040 |
| atgttcggtt tcttcttcac ggaaggaccc gtctatgatt tctcggatgc aaagaagagt | 2100 |
| gatacagaga agtttggaaa gttttttcaga ggaatgttgg aagaaggtgt ctacttggca | 2160 |
| ccttctcaat tcgaggccgg ttttactagc ttggctcaca cttcagaaga catccaattc | 2220 |
| actatcgcag cggccgagaa ggttctaagt cggctctaaa atgtctctgg aagcttccag | 2280 |
| ggaaccatga atgtatttga aatattttga tgtagagaaa attagattca attgagagca | 2340 |
| agcaagcaat ctcacaaaat ttaactgtgg taagaaaagt caaaatgtct atgaagattt | 2400 |
| gttgactttt taaaaa | 2416 |

<210> SEQ ID NO 6
<211> LENGTH: 1620
<212> TYPE: DNA
<213> ORGANISM: Hordeum vulgare (Barley)
<220> FEATURE:
<221> NAME/KEY: gene
<222> LOCATION: (19)..(1602)
<223> OTHER INFORMATION: nucleotide sequence of GSA
<300> PUBLICATION INFORMATION:
<308> DATABASE ACCESSION NUMBER: M31545
<309> DATABASE ENTRY DATE: 1994-10-06
<313> RELEVANT RESIDUES: (1)..(1620)

<400> SEQUENCE: 6

| | |
|---|---|
| gagaaggaag gcagcatcat ggccggagca gcagccgccg tggcctccgg catatcgatc | 60 |
| aggcctgtag ccgcgcctaa gatctcgcgc gcgccccgct ctcggtcggt ggtgagggcg | 120 |
| gccgtctcca tagacgagaa ggcttacacg gttcagaaat ccgaggagat cttcaacgcc | 180 |
| gccaaggaat tgatgcctgg tggtgttaat tcaccagtcc gtgccttcaa atcagtcggc | 240 |
| gggcagccca tagttttttga ttctgtgaag ggctctcata tgtgggatgt cgatggaaat | 300 |
| gaatatattg attatgttgg ttcctggggt cctgcaatca ttggtcatgc agatgacaag | 360 |
| gtgaatgctg cacttattga aactctgaag aagggtacta gctttggtgc tccatgtgcg | 420 |
| ttggagaatg tgttggctca aatggtcatc tccgctgtgc cgagtatcga atggttcgt | 480 |
| tttgtaaatt caggaacaga agcttgcatg ggagcactcc gccttgtgcg tgcattcact | 540 |
| gggagggaaa agattctcaa gtttgaaggc tgttaccatg gccatgcaga ttccttcctt | 600 |
| gttaaagcag gcagtggtgt tgccacccctc ggcctcccag actcccctgg agtgcctaag | 660 |
| ggagccaccg ttgggactct aacagcacct tataatgatg ctgatgcggt taaaaagctg | 720 |
| tttgaggata caaaggggga gattgctgca gtcttccttg agccggttgt tggcaatgct | 780 |
| ggcttcattc ctccgcagcc tgcttttccta aatgctctcc gtgaggtgac caaacaagac | 840 |
| ggtgcacttc tggtgtttga tgaagtgatg actggttttcc gtttagctta tggtggggca | 900 |
| caagagtact ttgaatcac ccctgatgtg acaaccttgg ggaaaattat tggcggtggt | 960 |
| cttccggttg gtgcttacgg tggacggaag gatatcatgg agatggttgc tccagcaggg | 1020 |
| ccaatgtacc aggcaggaac cctcagtgga aaccctctag ctatgactgc tggaatccac | 1080 |
| actctcaagc gtctgatgga gcctggcacc tatgaatact agacaaggt cactggtgaa | 1140 |
| cttgtccggg gcatattgga tgtgggcgct aaaacagggc acgagatgtg tggaggacac | 1200 |
| atcagaggca tgttcggatt cttcttcgca ggtggcccag tgcacaactt tgatgatgcc | 1260 |

-continued

```
aagaagagtg acacagcgaa gtttgggagg ttccaccgtg aatgctgggc cgaaggcgtg    1320
tatctggcac catcccagtt cgaggcaggt tttacaagct tggcacacac cacccaagac    1380
attgagaaaa ccgtggaggc tgccgagaag gttcttcgat ggatatagat gatttggatt    1440
gcaaaccttt tgaagctttt ccttctgttg tattctgtta gtttgtacgt ggctgaagtt    1500
tagttttgta ttgtattttg ttgtgcagca gcagtatctt gtctctagcc cattttttctt   1560 cttctgagtt agcatttggg gtgattttgt cttggcaata aactttggc tacgacctcc     1620
```

```
<210> SEQ ID NO 7
<211> LENGTH: 1224
<212> TYPE: DNA
<213> ORGANISM: Artificial
<220> FEATURE:
<223> OTHER INFORMATION: Sequence of hemA PCR product (without cloning
      clevage sites), cloned in pGEM3Zf

<400> SEQUENCE: 7
```

```
caggactaca atctggcact cgataccgct ctgaaccggc tccataccga gggccggtac     60
cggaccttca tcgacatcga gcggcgcaag ggtgccttcc cgaaagccat gtggcgcaag    120
cccgacggga gcgagaagga aatcaccgtc tggtgcggca acgactatct cggcatgggt    180
cagcatccgg tggtgctggg ggccatgcac gaggcgctgg attcgaccgg cgccgggtcg    240
ggcggcacgc gcaacatctc gggcaccacg ctctatcaca gcgcctcga ggccgagctc     300 gccgacctgc acgcaagga atcggcgctg gtcttctctt cggcctatat cgccaacgac    360
gcgaccctct cgacgctgcc gcagctgatc ccgggcctcg tcatcgtctc ggacaagttg    420
aaccacgctt cgatgatcga gggcatccgc cgctcgggca ccgagaagca catcttcaag    480
cacaatgacc tcgacgacct gcgccggatc ctgacctcga tcggcaagga ccgtccgatc    540
ctcgtggcct tcgagtccgt ctattcgatg gatggcgact tcggccgcat caaggaaatc    600
tgcgacatcg ccgacgagtt cggcgcgctg aaatacatcg acgaggtcca tgccgtcggc    660
atgtacggcc cccgcggcgg cggcgtggcc gagcgggacg ggctgatgga ccggatcgac    720
atcatcaacg ggacgctggg caaggcctat ggcgtgttcg gcggctatat cgcggcctcg    780
gccaagatgt gcgacgcggt gcgatcctac gcgccgggct tcatcttctc gacctcgctg    840
ccgcccgtcg tggcggccgg tgcggcggcc tcggtgcgcc acctcaaggg cgatgtggag    900
ctgcgcgaga agcaccagac ccaggcccgc atcctgaaga tgcgcctcaa ggggctcggc    960
ctgccgatca tcgaccacgg ctcgcacatc gtgccggtcc atgtgggcga ccccgtgcac   1020
tgcaagatga tctcggacat gctgctcgaa catttcggca tctatgtcca gccgatcaac   1080
ttccccacgg tgccgcgcgg gaccgaacgg ctgcgcttca cgccgtcgcc cgtgcatgat   1140
tccggcatga tcgaccatct cgtgaaggcc atggatgtgc tctggcagca ctgtgcgctg   1200
aatcgcgccg aggtcgttgc ctga                                           1224
```

```
<210> SEQ ID NO 8
<211> LENGTH: 4186
<212> TYPE: DNA
<213> ORGANISM: Artificial
<220> FEATURE:
<223> OTHER INFORMATION: sequence of plasmid vector pcva13

<400> SEQUENCE: 8
```

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
```

-continued

```
ttggcgggtg tcgggctgg cttaactatg cggcatcaga gcagattgta ctgagagtgc      180
accatacctg cacggcggcc gcgctggtgg caggatatat tgtggtgtaa acaaattcct    240
gcaggcaatt cactggattt tggttttagg aattagaaat tttattgata gaagtatttt    300
acaaatacaa atacatacta agggtttctt atatgctcaa cacatgagcg aaaccctata    360
agaaccctaa ttcccttatc tgggaactac tcacacatta ttatagagag agatagattt    420
gtagagagag actggtgatt tcagcgtcag atctgggtaa ctggcctaac tggccttgga    480
ggagctggca actcaaaatc cctttgccaa aaccaacat catgccatcc accatgcttg      540
tatccagctg cgcgcaatgt accccgggct gtgtatccca aagcctcatg caacctaaca    600
gatggatcgt ttggaaggcc tataacagca accacagact taaaaccttg cgcctccata    660
gacttaagca aatgtgtgta caatgtggat cctaggccca acctttgatg cctatgtgac    720
acgtaaacag tactctcaac tgtccaatcg taagcgttcc tagccttcca gggcccagcg    780
taagcaatac cagccacaac ccctcaacc tcagcaacca accaagggta tctatcttgc      840
aacctctcta gatcatcaat ccactcttgt ggtgtttgtg gctctgtcct aaagttcact    900
gtagacgtct caatgtaatg gttaacgata tcacaaaccg cggccatatc agctgctgta    960
gctggcctaa tctcaactgg tctcctctcc ggagacatgg tggatcccg gcctgtcctc     1020
tccaaatgaa atgaacttcc ttatatagag gaagggtctt gcgaaggata gtgggattgt    1080
gcgtcatccc ttacgtcagt ggagatatca catcaatcca cttgctttga agacgtggtt    1140
ggaacgtctt cttttccac gatgctcctc gtgggtgggg gtccatcttt gggaccactg      1200
tcggcagagg catcttcaac gatggccttt cctttatcgc aatgatggca tttgtaggag    1260
ccaccttcct tttccactat cttcacaata aagtgacaga tagctgggca atggaatccg    1320
aggaggtttc cggatattac cctttgttga aaagtctcaa ttgccctttg gtcttctgag    1380
actgtatctt tgatatttt ggagtagaca agcgtgtcgt gctccaccat gttgacgaag      1440
attttcttct tgtcattgag tcgtaagaga ctctgtatga actgttcgcc agtctttacg    1500
gcgagttctg ttaggtcctc tatttgaatc tttgactcca tgggaattgg tacctacgta    1560
tgcatggcgc gccatatgcc cgggccctgt acagcggccg gccgcgttaa cgcgtatact    1620
ctagagcgat cgcaggcttg cttttccatt attttgcgca acaagtcacg gatattcgtg    1680
aaaacgacaa aaactgcgaa atttgcgggc agtgccttca gttttcctat taatatttag    1740
tttgacacca gttgctatca ttgcggccaa gctcaggatc agattgtcgt ttcccgcctt    1800
cggtttaaac tatcagtgtt tgacaggata tattggcggg taaacctaag agaaaagagc    1860
gtttattaga ataatcggat atttaaaagg gcgtgaaaag gtttatccgt tcgtccattt    1920
gtatgtgcat gcaagctagc ggccgctagc ttggcgtaat catggtcata gctgtttcct    1980
gtgtgaaatt gttatccgct cacaattcca cacaacatac gagccggaag cataaagtgt    2040
aaagcctggg gtgcctaatg agtgagctaa ctcacattaa ttgcgttgcg ctcactgccc    2100
gctttccagt cgggaaacct gtcgtgccag ctgcattaat gaatcggcca acgcgcgggg    2160
agaggcggtt tgcgtattgg gcgctcttcc gcttcctcgc tcactgactc gctgcgctcg    2220
gtcgttcggc tgcggcgagc ggtatcagct cactcaaagg cggtaatacg ttatccaca     2280
gaatcagggg ataacgcagg aaagaacatg tgagcaaaag gccagcaaaa ggccaggaac    2340
cgtaaaaagg ccgcgttgct ggcgtttttc cataggctcc gcccccctga cgagcatcac    2400
aaaaatcgac gctcaagtca gaggtggcga aacccgacag gactataaag ataccaggcg    2460
```

-continued

| | |
|---|---|
| tttccccctg gaagctccct cgtgcgctct cctgttccga ccctgccgct taccggatac | 2520 |
| ctgtccgcct ttctcccttc gggaagcgtg gcgctttctc aaagctcacg ctgtaggtat | 2580 |
| ctcagttcgg tgtaggtcgt tcgctccaag ctgggctgtg tgcacgaacc cccgttcag | 2640 |
| cccgaccgct gcgccttatc cggtaactat cgtcttgagt ccaacccggt aagacacgac | 2700 |
| ttatcgccac tggcagcagc cactggtaac aggattagca gagcgaggta tgtaggcggt | 2760 |
| gctacagagt tcttgaagtg gtggcctaac tacggctaca ctagaagaac agtatttggt | 2820 |
| atctgcgctc tgctgaagcc agttaccttc ggaaaagag ttggtagctc ttgatccggc | 2880 |
| aaacaaacca ccgctggtag cggtggtttt tttgtttgca agcagcagat tacgcgcaga | 2940 |
| aaaaaggat ctcaagaaga tcctttgatc ttttctacgg ggtctgacgc tcagtggaac | 3000 |
| gaaaactcac gttaagggat tttggtcatg agattatcaa aaggatctt cacctagatc | 3060 |
| cttttaaatt aaaaatgaag ttttaaatca atctaaagta tatatgagta aacttggtct | 3120 |
| gacagttacc aatgcttaat cagtgaggca cctatctcag cgatctgtct atttcgttca | 3180 |
| tccatagttg cctgactccc cgtcgtgtag ataactacga tacgggaggg cttaccatct | 3240 |
| ggccccagtg ctgcaatgat accgcgagac ccacgctcac cggctccaga tttatcagca | 3300 |
| ataaccagc cagccggaag ggccgagcgc agaagtggtc ctgcaacttt atccgcctcc | 3360 |
| atccagtcta ttaattgttg ccgggaagct agagtaagta gttcgccagt taatagtttg | 3420 |
| cgcaacgttg ttgccattgc tacaggcatc gtggtgtcac gctcgtcgtt tggtatggct | 3480 |
| tcattcagct ccggttccca acgatcaagg cgagttacat gatcccccat gttgtgcaaa | 3540 |
| aaagcggtta gctccttcgg tcctccgatc gttgtcagaa gtaagttggc cgcagtgtta | 3600 |
| tcactcatgg ttatggcagc actgcataat tctcttactg tcatgccatc cgtaagatgc | 3660 |
| ttttctgtga ctggtgagta ctcaaccaag tcattctgag aatagtgtat gcggcgaccg | 3720 |
| agttgctctt gcccggcgtc aatacgggat aataccgcgc cacatagcag aactttaaaa | 3780 |
| gtgctcatca ttggaaaacg ttcttcgggg cgaaaactct caaggatctt accgctgttg | 3840 |
| agatccagtt cgatgtaacc cactcgtgca cccaactgat cttcagcatc ttttactttc | 3900 |
| accagcgttt ctgggtgagc aaaaacagga aggcaaaatg ccgcaaaaaa gggaataagg | 3960 |
| gcgacacgga aatgttgaat actcatactc ttccttttc aatattattg aagcatttat | 4020 |
| cagggttatt gtctcatgag cggatacata tttgaatgta tttagaaaaa taaacaaata | 4080 |
| ggggttccgc gcacatttcc ccgaaaagtg ccacctgacg tctaagaaac cattattatc | 4140 |
| atgacattaa cctataaaaa taggcgtatc acgaggccct ttcgtc | 4186 |

<210> SEQ ID NO 9
<211> LENGTH: 32
<212> TYPE: DNA
<213> ORGANISM: Artificial
<220> FEATURE:
<223> OTHER INFORMATION: primer ALAS1

<400> SEQUENCE: 9
gactgtgcat gcaggactac aatctggcac tc 32

<210> SEQ ID NO 10
<211> LENGTH: 30
<212> TYPE: DNA
<213> ORGANISM: Artificial

-continued

```
<220> FEATURE:
<223> OTHER INFORMATION: primer ALAS2

<400> SEQUENCE: 10
ctgactctgc agtcaggcaa cgacctcggc                                          30
```